United States Patent [19]

Ohmori et al.

[11] Patent Number: 5,686,482
[45] Date of Patent: Nov. 11, 1997

[54] N-(3-PYRROLIDINYL) BENZAMIDE DERIVATIVE

[75] Inventors: Junya Ohmori; Kyoichi Maeno, both of Ibaraki; Kazuyuki Hidaka, Chiba; Kazuhiro Nakato, Ibaraki; Shuichi Sakamoto, Ibaraki; Shin-ichi Tsukamoto, Ibaraki, all of Japan

[73] Assignee: Yamanouchi Pharmaceutical Co., Ltd., Tokyo, Japan

[21] Appl. No.: 718,576

[22] PCT Filed: Apr. 26, 1995

[86] PCT No.: PCT/JP95/00818

§ 371 Date: Oct. 2, 1996

§ 102(e) Date: Oct. 2, 1996

[87] PCT Pub. No.: WO95/29891

PCT Pub. Date: Nov. 9, 1995

[30] Foreign Application Priority Data

Apr. 28, 1994 [JP] Japan .................................. 6-090922

[51] Int. Cl.$^6$ .................. C07D 207/06; A61K 31/40
[52] U.S. Cl. ................... 514/426; 548/529; 548/557
[58] Field of Search ........................ 548/529, 557; 514/426

[56] References Cited

U.S. PATENT DOCUMENTS

| 3,966,957 | 6/1976 | Cale, Jr. et al. | 424/274 |
| 4,109,005 | 8/1978 | Lunsford et al. | 424/274 |

*Primary Examiner*—Joseph McKane
*Attorney, Agent, or Firm*—Sughrue, Mion, Zinn, Macpeak & Seas, PLLC

[57] ABSTRACT

N-(3-Pyrrodinyl)benzamide derivatives represented by the following general formula (I) which have potent and selective antagonism against dopamine $D_3$ and/or $D_4$ receptor and are useful as a psychotropic, a schizophrenia-treating agent and the like, or a pharmaceutically acceptable salt thereof or a pharmaceutical preparation thereof.

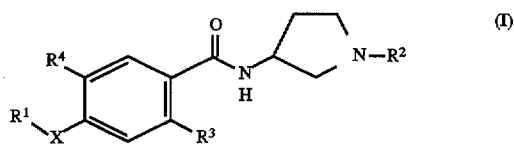

12 Claims, No Drawings

N-(3-PYRROLIDINYL) BENZAMIDE DERIVATIVE

This application is a 371 of PCT/JP95/00818 filed Apr. 26, 1995 published as WO95/29891 Nov. 9, 1995.

TECHNICAL FIELD

This invention relates to N-(3-pyrrolidinyl)benzamide derivatives, or a pharmaceutically acceptable salt thereof, which have selective and high affinity for dopamine $D_3$ (to be referred to as $D_3$ hereinafter) receptor and/or dopamine $D_4$ (to be referred to as $D_4$ hereinafter) receptor and weak action upon dopamine $D_2$ (to be referred to as $D_2$ hereinafter) receptor. It also relates to $D_3$ receptor and/or $D_4$ receptor antagonists which contain N-(3-pyrrolidinyl) benzamide derivatives or a pharmaceutically acceptable salt thereof as their active ingredient.

BACKGROUND ART

Dopamine, i.e., 4-(2-aminoethyl)-1,2-benzenediol, takes markedly varied and important roles in the central nervous system and peripheral nervous system. In the conventional studies, dopamine receptor has been classified into $D_1$ like receptor and $D_2$ like receptor based on a pharmacological classification. The $D_2$ like receptor is deeply related to mental functions and locomotive functions, and a number of drugs which act upon this type of receptor are used mainly as psychotropic agents for use in the treatment of schizophrenia, depression and other mental diseases/ Typical examples of such drugs include haloperidol, sulpiride and the like. However, though these drugs show excellent effects upon symptoms which are called positive symptoms of schizophrenia (e.g., psychomotor excitement, hallucination, delusion and the like), their effects are not sufficient for the patients of chronic schizomycosis mainly having negative symptoms such as lack of spontaneity, disappearance of interest, flattening of affect and the like. In addition, these drugs are accompanied by adverse side effects, though the degree varies. Typical examples of such side effects are so-called extrapyramidal symptoms in which diskinetic disorders are mainly generated, such as dystonia, Parkinson disease-like symptoms and akathisia which occur in a relatively acute manner with a relatively high frequency, and intractable tardive dyskinesia which is generated after prolonged administration.

In addition to the above, endocrine symptoms such as hyperprolactinemia, amenorrhea and the like are also developed.

It is considered in general that the psychotropic action, which is the main action of these drugs, is based on an action mediated by the $D_2$ like receptor which is present in the frontal cortex and limbic system, the extrapyramidal symptoms as side effects are based on an action mediated by the $D_2$ like receptor which is present in the striate body and the endocrine symptom-based side effects are based on an action mediated by the $D_2$ like receptor which is present in the anterior lobe of hypophysis (Baldessarini, R. L., "*Drugs and the treatment of psychiatric disorders*" in Gilman, A. G. et al., eds. "*The Pharmacological Basis of Therapeutics 8th Ed.*", Pergamon Press, New York, 1990, pp. 383–435).

With the development of genetic engineering in recent years, new dopamine receptor subtypes have been discovered, and the dopamine receptor has been re-classified into five subtypes of $D_1$ to $D_5$ receptors having different constituting amino acid sequences. Thus, it was revealed that the $D_2$ like receptor based on the conventional pharmacological classification is a subfamily which includes the $D_2$ receptor and newly discovered $D_3$ receptor and $D_4$ receptor, and the $D_1$ like receptor is a subfamily which includes the $D_1$ receptor and $D_5$ receptor [David R. et al., *Trends in Pharmacological Science* 13, 61–69 (1992)].

It is also known that the $D_2$, $D_3$ and $D_4$ receptors belonging to the $D_2$ like receptor subfamily have characteristic differences in terms of their intracerebral distribution [Bouthenet M-L. et al., *Brain Res.*, 564, 203–219 (1991), Gehlert D. et al., *Eur. J. Pharmacol.*, 211, 189–194 (1992) and Van Tol H. H. M. et al., *Nature*, 350, 610 (1991)]. The $D_2$ receptor is distributed particularly frequently in the striate body which relates to the onset of extrapyramidal symptoms as a main side effect and also relatively frequently in the nucleus accumbens and olfactory tuberculum or in the pituitary body which relates to the onset of endocrine symptoms, but its distribution in the brain cortex which relates to mental functions is relatively rare. On the other hand, the $D_3$ receptor is distributed most frequently in the limbic system and also distributed in the nucleus accumbens, olfactory tuberculum, hippocampus, medial papillary nucleus, tegmentum ventral mesencephali which are considered to be related to cognition function and emotion, and the 10th lobe of the cerebellum, but is rare in the striate body and not detectable in the pituitary body. The $D_4$ receptor is frequently distributed in the frontal cortex which are considered to have most deeper relation with schizophrenia through the regulation of higher mental function in human and amygdala, but its distribution in the striate body is very small. As a case in which schizophrenia is related to the $D_4$ receptor [Taubes G., *Science*, 265, 1034 (1994)], it has been reported that concentration of the $D_4$ receptor in schizophrenia patients was about 6 times higher than the case of healthy persons [Seeman P. et al., *Nature*, 365, 441 (1993)].

On the other hand, actions of existing antipsychotic agent upon $D_3$ and/or $D_4$ receptor have also been revealed, and it is considered that pharmacological characteristics of each drug are based on the difference in its efficacy and selectivity for respective $D_2$, $D_3$ and $D_4$ subtype receptors [Soholoff P., *Nature*, 347, 146–151 (1990) and Lahti R. A., *Eur. J. of Pharmacology*, 236, 483 (1993)]. That is, a drug having highly frequent onset of side effects (e.g., extrapyramidal symptoms), such as haloperidol, has high affinity for $D_2$ receptor in comparison with $D_3$ receptor and/or $D_4$ receptor. Also, in the case of drug which is classified as an atypical antipsychotic agent (e.g., sulpiride), has relatively small side effects such as extrapyramidal symptoms and the like, and shows certain degree of effects on negative symptoms, its affinity for $D_3$ and/or $D_4$ receptor is similar to its affinity for $D_2$ receptor. In the case of clozapine which is classified as an atypical antipsychotic agent, has small extrapyramidal symptoms and is effective for patients mainly having negative symptoms which are resistant against conventional antipsychotic agent, its affinity for $D_4$ receptor is higher than its affinity for $D_2$ receptor (its affinity for $D_4$ receptor is several times higher than that for $D_2$ receptor). As an example which suggests that the anti-schizophrenic action of clozapine is based on its action upon Dreceptor, it has been reported that effective blood concentration in a clinical dose of clozapine coincided well with a value derived from the $D_4$ receptor affinity rather than from the $D_2$ receptor affinity [Arnt J., in "*Dopamine Receptors vol. 8*" Liss, New York, 1987, pp. 199–231, Kane J. et al., *Arch. Gen. Psychiat.*, 45, 789 (1988), Casey D. E., *Psychopharmacology*, 99, 547 (1989), Seeman P., *Neuropsychopharmacology*, 7, 261 (1992)].

These findings strongly suggest that psychotropic actions including improvement of negative symptoms are developed via the $D_3$ and/or $D_4$ receptor, and side effects such as extrapyramidal symptoms and the like are generated via the $D_2$ receptor [Taubes G., Science, 265, 1034 (1994)].

As is evident from the aforementioned findings, it is an important subject from the clinical viewpoint to create a drug which is free from side effects such as extrapyramidal symptoms, endocrine symptoms and the like and has excellent psychotropic actions including actions to improve negative symptoms of schizophrenia.

On the other hand, compounds disclosed in an unexamined published Japanese patent application (kokai) No. 53-139728, an unexamined published Japanese patent application (kokai) No. 53-92763, an unexamined published Japanese patent application (kokai) No. 54-138553, an unexamined published Japanese patent application (kokai) No. 57-2266 and Journal of Medicinal Chemistry, 24, 1224 (1981) are known as N-(3-pyrrolidinyl)benzamide derivatives, but the affinity for both $D_3$ receptor and $D_4$ receptor is not suggested or disclosed.

In addition, though compounds having affinity for the $D_3$ receptor are disclosed in EP-A-0539281 and WO 94/03426 pamphlet, not only their structures are clearly different from that of the compounds of the present invention but also their affinity for the $D_4$ receptor and $D_2$ receptor is not disclosed illustratively.

DISCLOSURE OF THE INVENTION

It is an object of the present invention to provide compounds which have more potent and selective affinity for the $D_3$ receptor and/or $D_4$ receptor in comparison with the affinity of clozapine, thereby showing excellent central functions and/or peripheral functions including actions to improve negative symptoms of schizophrenia, and is free from or has remarkably reduced side effects such as extrapyramidal symptoms, endocrine symptoms based on its action upon the $D_2$ receptor.

Another object of the present invention is to provide $D_3$ receptor and/or $D_4$ receptor antagonists which use compounds represented by a general formula (I) that will be described later, as their active ingredient.

The inventors of the present invention have created various compounds and conducted screening works and, as a result, found that novel compounds whose chemical structures are different from those of prior art compounds in terms of a point that the N-(3-pyrrolidinyl)benzamides have an pyrrolidin-3-yl group of which 1-position is substituted with a bicyclic or tricyclic bridged hydrocarbon ring group.

Thereafter, the present invention was accomplished by revealing that the N-(3-pyrrolidinyl)benzamide derivatives of the present invention or a pharmaceutically acceptable salt thereof have high selectivity and potent affinity for the $D_3$ receptor and/or $D_4$ receptor and extremely weak action upon the $D_2$ receptor and by predicting that the invention compound can exert psychotropic actions against diseases such as schizophrenia, emotional disorder, anxiety, sleep disorder, organic mental disorder, drug abuse, personality disorder and the like, and central and/or peripheral actions against diseases which are accompanied by difficulty of moving (e.g., Parkinson disease), as well as sexual disorder, pain, vomiting, hypertension, urination, diarrhea, digestive organ indefinite complaint and the like, while side effects such as extrapyramidal symptoms, endocrine symptoms and the like are not generated or remarkably reduced, so that the clinical object can be achieved. In consequence, it is possible to apply the compounds of the present invention as therapeutic drugs to patients who have difficulty in using drugs because of a possible danger of causing side effects, for example senile and child patients.

Accordingly, the present invention relates to a novel N-(3-pyrrolidinyl)benzamide derivative represented by a general formula (I), or a pharmaceutically acceptable salt thereof,

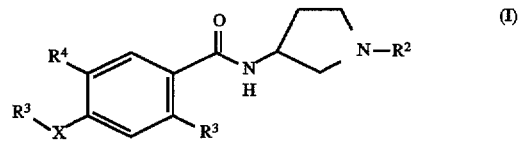

wherein each symbol in the formula has the following meaning, $R^1$: a hydrogen atom, a lower alkyl group, an aralkyl group or a cycloalkyl or cycloalkyl-lower alkyl group having 3 to 8 ring atoms, $R^2$: a bicyclic or tricyclic bridged hydrocarbon ring group having 4 to 16 ring atoms, which may have a lower alkyl group(s), $R^3$: a lower alkoxy group, an amino group or a mono- or di-lower alkylamino group, $R^4$: a hydrogen atom, a halogen atom, a lower alkyl group which may have a hydroxyl group, a lower alkoxy group, a cyano group, a nitro group, an amino group, a mono- or di-lower alkylamino group, an acyl group or a group represented by $—S(O)_m—R^5$, $R^5$: a lower alkyl group, an amino group or a mono- or di-lower alkylamino group, m: 0, 1 or 2, X: a bond or a group represented by $—O—$, $—S(O)_n—$, $—NH—$ or $—CONH—$, and n: 0, 1 or 2, with the proviso that, when $R^1$ is a cycloalkyl group, the cases wherein X is a group represented by $—CONH—$, $R^3$ is a lower alkoxy group and $R^4$ is a halogen atom are excluded.

Particularly preferred among the compounds of the present invention is a compound or a pharmaceutically acceptable salt thereof in which the group $R^1$ is a lower alkyl group or a cycloalkyl or cycloalkyl-lower alkyl group having 3 to 8 ring atoms, the group $R^3$ is a lower alkoxy group and the group $R^4$ is a halogen atom, a cyano group or a nitro group.

Further preferred compound of the present invention is compounds or a pharmaceutically acceptable salt thereof in which the group $R^2$ is bicyclononyl group or adamantyl group.

The present invention also relates to a pharmaceutical composition which comprises N-(3-pyrrolidinyl)benzamide derivatives represented by the aforementioned general formula (I) or a pharmaceutically acceptable salt thereof and a pharmaceutically acceptable carrier, as well as $D_3$ and/or $D_4$ receptor antagonists which comprise said N-(3-pyrrolidinyl) benzamide derivatives or a pharmaceutically acceptable salt thereof as an active ingredient.

Preferably, the just described pharmaceutical compositions or antagonists are pharmaceutical compositions which comprise compounds or a pharmaceutically acceptable salt thereof wherein, in the aforementioned general formula (I), the group $R^1$ is a lower alkyl group or a cycloalkyl or cycloalkyl-lower alkyl group having 3 to 8 ring atoms, the group $R^3$ is a lower alkoxy group and the group $R^4$ is a halogen atom, a cyano group or a nitro group, or $D_3$ and/or $D_4$ receptor antagonists which contain the same as an active ingredient.

More preferred pharmaceutical compositions or antagonists are a pharmaceutical composition which comprise compounds or a pharmaceutically acceptable salt thereof wherein the group $R^2$ is a bicyclononyl group or an adamantyl group, or $D_3$ and/or $D_4$ receptor antagonists which contain the same as an active ingredient.

The following describes the compound of the present invention in detail.

The term "lower" as used herein means a straight or branched carbon chain having 1 to 6 carbon atoms.

In consequence, examples of the "lower alkyl group" include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-2-methylpropyl and the like.

Of these groups, $C_1$–$C_4$ alkyl groups, particularly $C_1$–$C_3$ alkyl groups are preferred.

Examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which methoxy group is particularly preferred.

Examples of the "halogen atom" include a fluorine atom, a chlorine atom, a bromine atom, an iodine atom and the like, of which chlorine and bromine atoms are particularly preferred.

The "cycloalkyl group" is those having 3 to 8 carbon atoms, and its illustrative examples include cyclopropyl, cyclobutyl, cyclopentyl, cyclohexyl, cycloheptyl and cyclooctyl.

The term "cycloalkyl-lower alkyl group" means a group in which the aforementioned "lower alkyl group" is substituted with the aforementioned "cycloalkyl group".

The term "aralkyl group" means a group in which an optional hydrogen atom of the aforementioned "lower alkyl group" is substituted with an "aryl group" such as phenyl, naphthyl or the like. When phenyl or naphthyl is employed as the example of the aryl group, its illustrative examples include benzyl, phenetyl, 1-phenylethyl, 3-phenylpropyl, 2-phenylpropyl, 1-phenylpropyl, 1-methyl-2-phenylethyl, 4-phenylbutyl, 3-phenylbutyl, 2-phenylbutyl, 1-phenylbutyl, 2-methyl-3-phenylpropyl, 2-methyl-2-phenylpropyl, 2-methyl-1-phenylpropyl, 1-methyl-3-phenylpropyl, 1-methyl-2-phenylpropyl, 1-methyl-1-phenylpropyl, 1-ethyl-2-phenylethyl, 1,1-dimethyl-2-phenylethyl, 5-phenylpentyl, 4-phenylpentyl, 3-phenylpentyl, 2-phenylpentyl, 1-phenylpentyl, 3-methyl-4-phenylbutyl, 3-methyl-3-phenylbutyl, 3-methyl-2-phenylbutyl, 3-methyl-1-phenylbutyl, 6-phenylhexyl, 5-phenylhexyl, 4-phenylhexyl, 3-phenylhexyl, 2-phenylhexyl, 1-phenylhexyl, 4-methyl-5-phenylpentyl, 4-methyl-4-phenylpentyl, 4-methyl-3-phenylpentyl, 4-methyl-2-phenylpentyl, 4-methyl-1-phenylpentyl, 1-naphthylmethyl, 2-naphthylmethyl, 2-(1-naphthyl)ethyl, 2-(2-naphthyl)ethyl, 1-(1-naphthyl)ethyl, 1-(2-naphthyl)ethyl, 3-(1-naphthyl)propyl, 3-(2-naphthyl)propyl, 2-(1-naphthyl)propyl, 2-(2-naphthyl)propyl, 1-(1-naphthyl)propyl, 1-(2-naphthyl)propyl, 1-methyl-2-(1-naphthyl)ethyl, 1-methyl-2-(2-naphthyl)ethyl, 4-(1-naphthyl)butyl, 4-(2-naphthyl)butyl, 3-(1-naphthyl)butyl, 3-(2-naphthyl)butyl, 2-(1-naphthyl)butyl, 2-(2-naphthyl)butyl, 1-(1-naphthyl)butyl, 1-(2-naphthyl)butyl, 2-methyl-3-(1-naphthyl)propyl, 2-methyl-3-(2-naphthyl)propyl, 2-methyl-2-(1-naphthyl)propyl, 2-methyl-2-(2-naphthyl)propyl, 2-methyl-1-(1-naphthyl)propyl, 2-methyl-1-(2-naphthyl)propyl, 5-(1-naphthyl)pentyl, 5-(2-naphthyl)pentyl, 4-(1-naphthyl)pentyl, 4-(2-naphthyl)pentyl, 3-methyl-4-(1-naphthyl)butyl, 3-methyl-4-(2-naphthyl)butyl, 6-(1-naphthyl)hexyl, 6-(2-naphthyl)hexyl, 5-(1-naphthyl)hexyl, 5-(2-naphthyl)hexyl, 4-methyl-5-(1-naphthyl)pentyl, 4-methyl-5-(2-naphthyl)pentyl, diphenylmethyl (benzhydryl), triphenylmethyl (trityl) and the like.

With regard to the "bicyclic or tricyclic bridged hydrocarbon ring group having 4 to 16 ring atoms, which may have a lower alkyl group(s)", a saturated or unsaturated bicyclic or tricyclic bridged hydrocarbon ring group consisting of 2 or 3 cycloalkyl rings of 3 to 8 carbon atoms is preferred, and its illustrative examples include bicyclo[2.1.1]hexyl, bicyclo[3.1.1]heptyl, bicyclo[2.2.2]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, adamantyl, noradamantyl (tricyclo[3.3.1.0$^{3.7}$] nonyl), tricyclo[7.3.2.0$^{5.13}$]tetradecyl and the like. Of these groups, bicyclo[3.3.1]nonyl and adamantyl are preferred.

The term "mono- or di-lower alkylamino group" as used herein means a group in which 1 or 2 hydrogen atoms of an amino group is substituted with the aforementioned "lower alkyl group". The illustrative examples include monoalkylamino groups substituted with a straight or branched alkyl group having 1 to 6 carbon atoms, such as methylamino, ethylamino, propylamino, isopropylamino, butylamino, isobutylamino, pentylamino, isopentylamino, hexylamino, isohexylamino and the like, symmetric dialkylamino groups di-substituted with a straight or branched alkyl group having 1 to 6 carbon atoms, such as dimethylamino, diethylamino, dipropylamino, diisopropylamino, dibutylamino, dipentylamino, dihexylamino and the like, and asymmetric dialkylamino groups di-substituted with alkyl groups which are different from each other and selected from straight or branched alkyl groups each having 1 to 6 carbon atoms, such as ethylmethylamino, methylpropylamino, ethylpropylamino, butylmethylamino, butylethylamino, butylpropylamino and the like.

Examples of the "acyl group" include lower alkanoyl groups and arylcarbonyl group, and examples of the lower alkanoyl group include formyl, acetyl, propionyl, butylyl, isobutylyl, valeryl, isovaleryl, pivaloyl, hexanoyl and the like and examples of the arylcarbonyl group include benzoyl, naphthoyl and the like.

Some members of the compound (I) of the present invention may form acid addition salts. Pharmaceutically acceptable salts of the compound (I) are included in the present invention, and examples of such salts include acid addition salts with inorganic acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, toluenesulfonic acid, glutamic acid, aspartic acid and the like.

Also, since the compound of the present invention contains asymmetric carbon atoms, it exists in the form of optical isomers (optical antipode, racemic modification, diastereomer) based thereon. The compound of the present invention also exists in the form of endo-exo isomers based on the presence of bridged rings. All of these isomers as mixtures or isolated forms are included in the present invention.

In addition, the compound of the present invention is sometimes isolated as a hydrate, various types of solvates or a polymorphic substance, and these substances are also included in the present invention.

The following compounds are particularly preferred examples of the compound of the present invention. 1. N-[1-(Bicyclo[3.3.1]non-9-yl)-3-pyrrolidinyl]-2,4-dimethoxy-5-nitrobenzamide or pharmaceutically acceptable salts thereof or optical isomers thereof. 2. N-[1-(Bicyclo[3.3.1]non-9-yl)-3-pyrrolidinyl]-2-methoxy-4-methyl-5-nitrobenzamide or pharmaceutically acceptable salts thereof or optical isomers thereof. 3. N-[1-(Bicyclo[3.3.1]non-9-yl)-3-pyrrolidinyl]-5-cyano-2,4-dimethoxybenzamide or pharmaceutically acceptable salts thereof or optical isomers thereof. 4. N-[1-(Bicyclo[3.3.1]non-9-yl)-3-pyrrolidinyl]-2,4-dimethoxy-5-methylaminobenzamide or pharmaceutically acceptable salts thereof or optical isomers thereof.

(Production Methods)

The compounds of the present invention can be produced by employing various synthetic methods. The following describes typical production methods.

Examples of suitable inert solvents to be used in the following description include methylene chloride, chloroform, dichloroethane, benzene, toluene, ether, hexane, tetrahydrofuran, dioxane, dimethylformamide, acetonitrile, dimethyl sulfoxide and the like.

Examples of suitable condensing agents include carbodiimide derivatives typically including N,N'-dicyclohexylcarbodiimide (as occasion demands, the reaction may be carried out by adding an additive agent such as 1-hydroxybenzotriazole, N-hydroxysuccinimide or the like), water soluble carbodiimides typically including 1-ethyl-3-(3-dimethylaminopropyl)carbodiimide hydrochloride, diphenylphosphoryl azide, azo derivatives typically including diethyl azodicarboxylate, with triphenylphosphine, N,N'-carbonyldiimidazole, benzotriazol-1-yloxytris (dimethylamino)phosphonium hexafluorophosphate and the like.

Examples of suitable inorganic bases include sodium hydride, sodium hydroxide, sodium bicarbonate, sodium carbonate, potassium hydroxide, potassium carbonate and the like and examples of suitable organic bases include pyridine, triethylamine, diisopropylethylamine, N,N'-dimethylaminopyridine, 1,8-diazabicyclo[5.4.0]undec-7-ene, 1,4-diazabicyclo[2.2.2]octane, butyl lithium, lithium bis(trimethylsilyl)amide and the like.

Suitable mineral acid includes hydrochloric acid, sulfuric acid and the like, suitable organic acid includes acetic acid, toluenesulfonic acid and the like and suitable Lewis acid includes aluminum chloride, titanium tetrachloride, orthotitanic acid isopropoxide and the like.

Examples of suitable catalyst include palladium, platinum and rhenium, each in powder form or being supported on a carrier, as well as Raney nickel and the like.

Examples of suitable metal hydride complex include sodium borohydride, sodium cyanoborohydride, sodium trimethoxyborohydride and the like.

Method 1

In this method, the N-(3-pyrrolidinyl)benzamide derivative (I) is produced by carrying out condensation reaction of a benzoic acid derivative represented by the following formula (II) or (III) with a 3-aminopyrrolidine derivative (IV).

Part 1) Condensation reaction of benzoic acid derivative (II) with 3-aminopyrrolidine derivative This reaction is effected according to the condensation of a carboxylic acid with an amine. In general, this reaction is carried out with cooling, at room temperature or with heating in the presence or absence of a suitable inert solvent and, if necessary, in the presence of a suitable condensation agent.

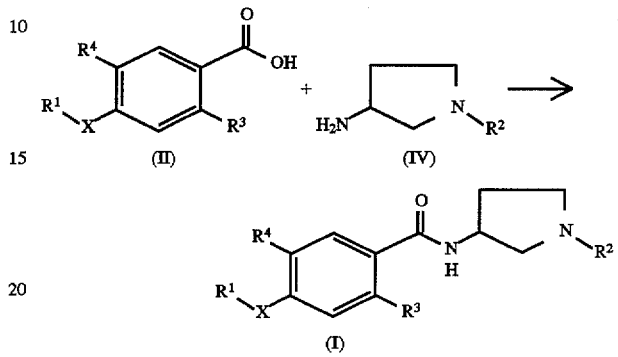

(In the above formulae, $R^1$, $R^2$, $R^3$, $R^4$ and X are as defined in the foregoing.)

Part 2) Reaction of 3-aminopyrrolidine derivative (IV) with a benzoyl halide, benzoyl azide, benzoic ester or benzoic anhydride represented by general formula (III)

This reaction is effected by the condensation of an amine with a reactive derivative of carboxylic acid, such as an acyl halide (e.g., a chloride, bromide or iodide), an acyl azide, an active ester or an acid anhydride. In general, this reaction is carried out under cooling, at room temperature or with heating in the presence or absence of a suitable inert solvent and, if necessary, by adding a suitable inorganic or organic base or by using a suitable organic base as both a solvent and an acid acceptor.

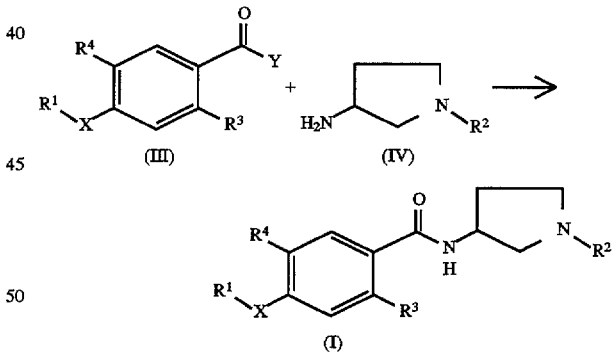

Method 2

In this method, the N-(3-pyrrolidinyl)benzamide derivative (I) is produced by introducing a substituent group to the nitrogen atom on the pyrrolidine nucleus of an N-(3-pyrrolidinyl)benzamide derivative (V).

Part 1) A production method by reductive alkylation reaction of N-(3-pyrrolidinyl)benzamide derivative (V) with an aldehyde or ketone represented by general formula (VI) corresponding to $R^2$ in the formula This reaction is effected by reductive alkylation of an amine. For example, this reaction may be carried out by stirring the N-(3-pyrrolidinyl)benzamide derivative (V) and an aldehyde or ketone represented by the general formula (VI) which corresponds to $R^2$ in the formula, in a suitable solvent (e.g., water, methanol, ethanol, ethyl acetate, methylene chloride, chloroform, dimethylformamide or acetic acid) in the presence of a suitable catalyst at room temperature or with heating under atmospheric hydrogen. As occasion demands, a suitable mineral acid, organic acid or Lewis acid may be added to the reaction system, or the reaction system may be pressurized. Alternatively, the reaction may be effected by a reaction with a suitable metal hydride complex in a suitable solvent (for example, methanol, ethanol, tetrahydrofuran, dioxane, benzene, toluene, hexane or dimethylformamide) under cooling, at room temperature or with heating. As occasion demands, a suitable mineral acid, organic acid or Lewis acid may be added to the reaction system.

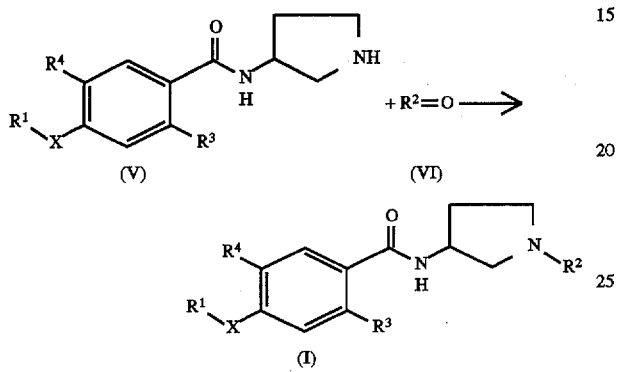

(In the above formulae, $R^1$, $R^2$, $R^3$, $R^4$ and X are as defined in the foregoing.)

Part 2) Reaction of N-(3-pyrrolidinyl)benzamide derivative (V) with a halide or sulfonate represented by general formula (VII)

This reaction may be carried out by allowing the N-(3-pyrrolidinyl)benzamide derivative (V) to react with a halide (e.g., chloride, bromide or iodide) or a sulfonate (e.g., p-toluene sulfonate, trifluoromethane sulfonate) represented by the general formula (VII) in the presence or absence of a suitable inert solvent under cooling, at room temperature or with heating and, if necessary, by adding a suitable inorganic or organic base as an acid acceptor or by using a suitable organic base as both a solvent and an acid acceptor.

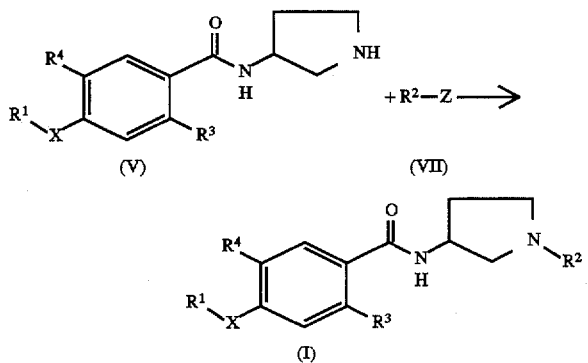

(In the above formulae, $R^1$, $R^2$, $R^3$, $R^4$ and X are as defined in the foregoing and Z means a halogen atom or an organic sulfonic acid residue.)

Method 3

In this method, the N-(3-pyrrolidinyl)benzamide derivative (I) is produced by constructing a pyrrolidine ring through cyclization condensation of an N-substituted benzamide derivative represented by a general formula (VIII), (IX), (X) or (XI).

Part 1) Intramolecular reductive alkylation of N-substituted benzamide derivative (VIII) or (IX)

This reaction is effected by conventional reductive alkylation of amine. For example, the reaction may be effected by stirring the compound (VIII) or (IX) in a suitable solvent (e.g., methanol, ethanol, ethyl acetate, dimethylformamide, acetic acid, methylene chloride or chloroform) in the presence of a suitable catalyst at room temperature, with cooling or with heating under atmospheric hydrogen. As occasion demands, a suitable mineral acid, organic acid or Lewis acid may be added to the reaction system or the reaction system may be pressurized.

Alternatively, the reaction may be effected by a reaction with a suitable metal hydride complex in a suitable solvent (e.g., methanol, ethanol, tetrahydrofuran, dioxane, benzene, toluene, hexane or dimethylformamide) under cooling, at room temperature or with heating. As occasion demands, a suitable mineral acid, organic acid or Lewis acid may be added to the reaction system.

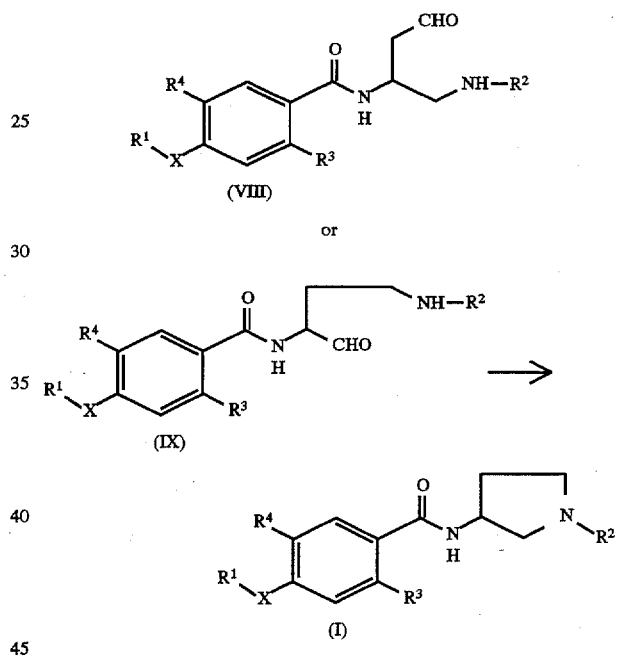

(In the above formulae, $R^1$, $R^2$, $R^3$, $R^4$ and X are as defined in the foregoing.)

Part 2) Intramolecular N-alkylation of N-substituted benzamide derivative (X) or (XI)

This reaction may be effected by carrying out intramolecular cyclization of an N-substituted benzamide derivative (X) or (XI) in the presence or absence of a suitable inert solvent under cooling, at room temperature or with heating and, if necessary, by adding a suitable inorganic or organic base as a deoxidizing agent or by using a suitable organic base as both a solvent and an acid acceptor.

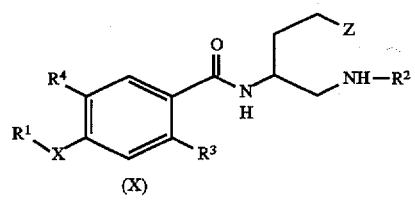

-continued
or

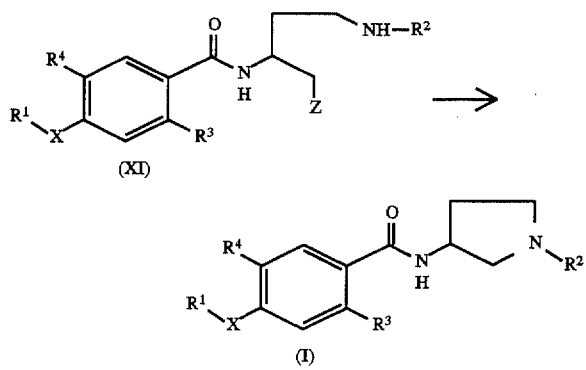

(In the above formulae, $R^1$, $R^2$, $R^3$, $R^4$, X and Z are as defined in the foregoing.)

Method 4

In this method, the N-(3-pyrrolidinyl)benzamide derivative (I) is produced by oxidizing, reducing, adding, substituting or hydrolyzing the substituent group A or B of an N-substituted benzamide derivative represented by a general formula (XII) or (XIII).

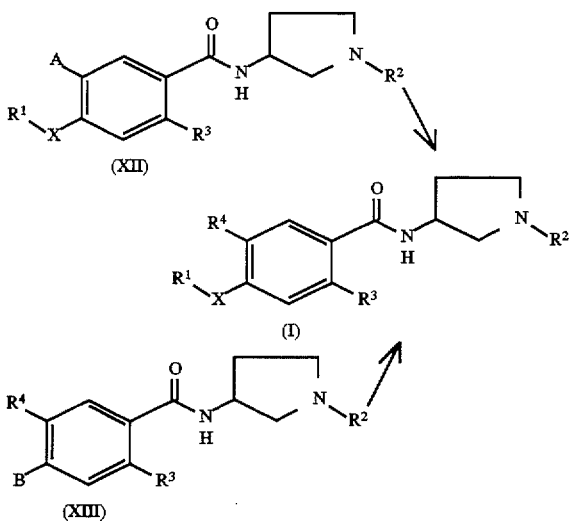

(In the above formulae, $R^1$, $R^2$, $R^3$, $R^4$ and X are as defined in the foregoing, and A or B independently represents a hydrogen atom, a halogen atom, an amino group, an alkylamino group, an acylamino group, a nitro group, a diazonium group, a hydroxyl group, a tosyloxy group, a trifluoromethanesulfonyl group, a mesyl group, an acyl group, a cyano group, an alkyl group, an alkenyl group, an alkynyl group, a formyl group, a carboxyl group, a thiol group, an alkylthio group, an alkylsulfonyl group, an alkylsulfoxyl group or a halogenosulfonyl group.)

In this connection, some novel substances are included in the starting compounds to be used in the aforementioned first to fourth production methods, and such substances can be produced by using corresponding known compounds as respective starting materials and by employing techniques such as amidation, reductive N-alkylation, N-alkylation, intramolecular reductive N-alkylation, intramolecular N-alkylation, oxidation, reduction, addition, substitution, hydrolysis and the like described in the Methods 1–4. Practical production of these substances may be effected in accordance with the Reference Examples which will be described later, or in accordance with the respective procedures described in the Reference Examples or by modifying them.

For example, the 3-aminopyrrolidine derivative represented by the general formula (IV) can be produced by allowing 3-protected aminopyrrolidine to react with a carbonyl, halogen or sulfonate compound represented by $R^2=O$ or $R^2=Z$ in the same manner as the case of the Method 2. Also, the starting compound (II) can be produced by applying techniques of the Methods 2–4, such as hydrolysis and nitration of corresponding ester, amination by reduction of nitro group, etherification or thioetherification of a halide or a compound having hydroxyl group or mercapto group, reductive N-alkylation or N-alkylation of a compound having amino group, oxidation of a thioether compound, conversion from amino group into halide and conversion from amino group into nitrile.

The compounds (I) of the present invention produced by these methods are isolated and purified in its free form or as a salt thereof. Isolation and purification can be effected by using usual chemical methods such as extraction, evaporation, crystallization, filtration, recrystallization, various types of chromatography and the like.

The thus obtained free compound or a salt thereof can be made into another salt by subjecting it to commonly used salt forming reaction.

In this connection, the compounds of the present invention contain optical isomers, because it has at least 1 asymmetric carbon atom.

These optical isomers can be separated in the usual way, for example, by carrying out a fractional crystallization in which each isomer is recrystallized with an appropriate salt or by a column chromatography. Alternatively, a desired optical isomer can be obtained from an appropriate optically active starting material.

The following illustrates compounds other than those which will be described in Examples, that can be synthesized in accordance with the aforementioned production methods, particularly the methods described in the Examples, or modified methods thereof known to those skilled in the art.

TABLE 1
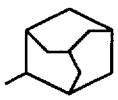
(I)
| Compound No. | R¹ | X | R² | R³ | R⁴ |
|---|---|---|---|---|---|
| 1 | H— | —NH— | 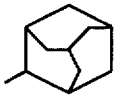 | MeO— | O₂N— |
| 2 | H— | —NH— | | MeO— | NC— |
| 3 | H— | —NH— |  | MeO— | NC— |
| 4 | Me— | —NH— | | MeO— | O₂N— |
| 5 | Et— | —NH— | | MeO— | O₂N— |
| 6 | ⁱPr— | —NH— | | MeO— | O₂N— |
| 7 | ᶜPr— | —NH— | | MeO— | O₂N— |
| 8 | ᶜPrCH₂— | —NH— | | MeO— | O₂N— |
| 9 | Me— | —NH— | 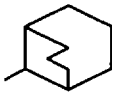 | MeO— | O₂N— |
| 10 | ⁿPr— | —NH— | | MeO— | O₂N— |
| 11 | ᶜPr— | —NH— | | MeO— | O₂N— |
| 12 | ᶜPrCH₂— | —NH— | | MeO— | O₂N— |
| 13 | Me | —CONH— | | MeO— | O₂N— |

TABLE 1-continued
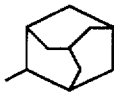
(I)
| Compound No. | R¹ | X | R² | R³ | R⁴ |
|---|---|---|---|---|---|
| 14 | Me | —CONH— | 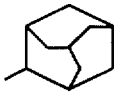 | MeO— | O₂N— |
| 15 | ᶜPr | —CONH— |  | MeO— | O₂N— |
| 16 | ᶜBu | —CONH— | 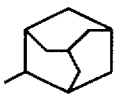 | MeO— | O₂N— |
| 17 | ᶜBu | —CONH— | 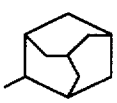 | MeO— | O₂N— |
| 18 | Me— | Bond | 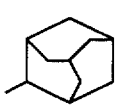 | MeO— | NC— |
| 19 | Me— | Bond | 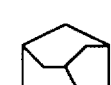 | MeO— | O₂N— |
| 20 | Me— | Bond | 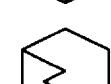 | MeO— | Cl— |
| 21 | Me— | Bond | 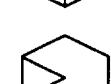 | MeO— | NC— |
| 22 | Me— | Bond | 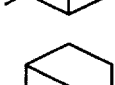 | MeO— | Cl— |
| 23 | Et— | Bond | 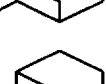 | MeO— | O₂N— |
| 24 | ⁿPr— | Bond | 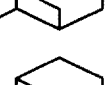 | MeO— | O₂N— |
| 25 | ⁿBu— | Bond | 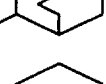 | MeO— | O₂N— |
| 26 | EtMeCH— | Bond | 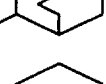 | MeO— | O₂N— |

TABLE 1-continued
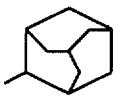
| Compound No. | R¹ | X | R² | R³ | R⁴ |
|---|---|---|---|---|---|
| 27 | Me— | Bond | 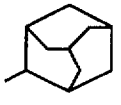 | MeO— | O₂N— |
| 28 | Et— | Bond | 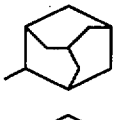 | MeO— | O₂N— |
| 29 | ⁿPr— | Bond | 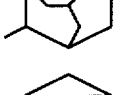 | MeO— | O₂N— |
| 30 | ⁿBu— | Bond | 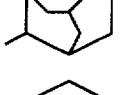 | MeO— | O₂N— |
| 31 | EtMeCH— | Bond | 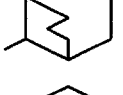 | MeO— | O₂N— |
| 32 | ᶜHex— | Bond | 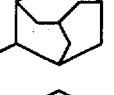 | MeO— | O₂N— |
| 33 | ᶜHex— | Bond | 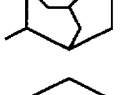 | MeO— | O₂N— |
| 34 | H— | —NH— | 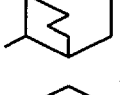 | MeO— | Cl— |
| 35 | H— | —NH— |  | EtO— | O₂N— |
| 36 | H— | —NH— |  | ⁿPrO— | O₂N— |
| 37 | H— | —NH— | 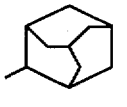 | ⁱPrO— | O₂N— |
| 38 | Me— | —O— | 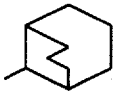 | MeO— | MeNH— |
| 39 | ⁿPr— | —O— | 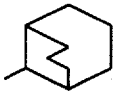 | MeO— | MeNH— |

TABLE 1-continued
$$\text{(I)}$$
| Compound No. | R¹ | X | R² | R³ | R⁴ |
|---|---|---|---|---|---|
| 40 | ᶜPrCH₂— | —O— | 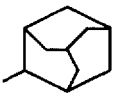 | MeO— | MeNH— |
| 41 | ⁿPr— | —O— | 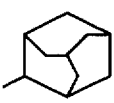 | MeO— | MeNH— |
| 42 | ᶜPrCH₂— | —O— |  | MeO— | MeNH— |
| 43 | ᶜHex— | —O— |  | MeO— | MeNH— |
| 44 | Me— | —O— | 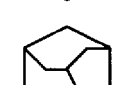 | MeO— | EtNH— |
| 45 | Me— | —O— | 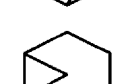 | MeO— | EtNH— |
| 46 | Me— | —O— | 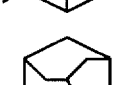 | MeO— | ⁱPrNH— |
| 47 | Me— | —O— | 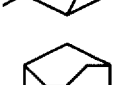 | MeO— | ⁱPrNH— |
| 48 | Me— | —O— | 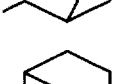 | MeO— | Me₂N— |
| 49 | ⁿPr— | —O— | 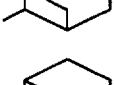 | MeO— | EtNH— |
| 50 | ⁿPr— | —O— | 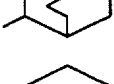 | MeO— | ⁱPrNH— |
| 51 | ⁿPr— | —O— | 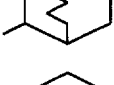 | MeO— | Me₂N— |
| 52 | ᶜPrCH₂— | —O— |  | MeO— | EtNH— |

TABLE 1-continued $$\text{(I)}$$

Structure: R⁴ and R¹-X substituted benzamide with -C(=O)-NH-CH(-)-CH₂-N-R² side chain (pyrrolidine), and R³ on the ring.

| Compound No. | R¹ | X | R² | R³ | R⁴ |
|---|---|---|---|---|---|
| 53 | ᶜPrCH₂— | —O— | (cubane-type structure) | MeO— | ⁱPrNH— |
| 54 | ᶜPrCH₂— | —O— | (cubane-type structure) | MeO— | Me₂N— |
| 55 | ⁿPr— | —O— | (adamantane-type structure) | MeO— | EtNH— |
| 56 | ⁿPr— | —O— | (adamantane-type structure) | MeO— | ⁱPrNH— |
| 57 | ⁿPr— | —O— | (adamantane-type structure) | MeO— | Me₂N— |
| 58 | ᶜPrCH₂— | —O— | (adamantane-type structure) | MeO— | EtNH— |
| 59 | ᶜPrCH₂— | —O— | (adamantane-type structure) | MeO— | ⁱPrNH— |
| 60 | ᶜPrCH₂— | —O— | (adamantane-type structure) | MeO— | Me₂N— |

In the above table, Me means methyl group, Et means ethyl group, ⁿPr means normal propyl group, ⁱPr means isopropyl group, ⁿBu means normal butyl group, ᶜPr means cyclopropyl group, ᶜBu means cyclobutyl group and ᶜHex means cyclohexyl group.

Industrial Applicability

Since the compound of the present invention has high affinity for the $D_3$ and/or $D_4$ receptor and low affinity for the $D_2$ receptor, it is useful as psychotropic having reduced or no side effects in relation to extrapyramidal symptoms and endocrine systems, particularly as drugs for the treatment of schizophrenia, feeling disorders, anxiety, psychomotor function disorders due to drug abuse, psychiatric disorders in child and puberty stages and problematic behavior of the aged, and as an analgesic or as drugs for use in the central dopamine nervous system-related diseases, such as an anti-Parkinson drug, an antiemetic and a feeding-controlling drug. It is also useful as a hypotensive drug or a diuretic, through a function mediated by a peripheral $D_3$ receptor (Sokoloff P., Nature, 347, 146–151 (1990)).

Affinity of the compound of the present invention for $D_2$ receptor, $D_3$ receptor and $D_4$ receptor was confirmed by the following test methods.

1) Affinity for $D_2$ receptor, $D_3$ receptor and $D_4$ receptor

Each of the $D_2$ receptor, $D_3$ receptor and $D_4$ receptor was subjected to gene cloning and the thus cloned gene was introduced into host cells, thereby preparing cell strains capable of expressing respective receptors (Sokoloff P. et al., Nature, 347, 146 (1990), Van Tol H. H. M. et al., Nature, 350, 610 (1994)). Using membrane samples of these cells, affinity of compounds for $D_2$ receptor, $D_3$ receptor and $D_4$ receptor was examined by a receptor binding test. The receptor binding test was carried out in the following manner. A $D_2$ receptor, $D_3$ receptor or $D_4$ receptor membrane sample and [$^{125}$I] iodosulpride or [$^3$H] YM-09151-2 (trade name, manufactured by Daiichi Pure Chemicals) were incubated at 25° C. for 1 hour in the presence of each compound to be tested. The reaction solution was filtered through a glass filter to measure the amount of radioisotope on the filter. Concentration of each test compound which inhibits 50% of the receptor specific binding was used as $IC_{50}$ value, and the value was converted into Ki value based on the formula of Cheng and Prusoff relationship [Cheng Y. et al., Biochem. Pharmacol., 22, 3099–3108, (1973)]. The results are shown in Table 2.

TABLE 2

| Compound | Binding test (Ki value, nM) | | | Ratio | |
|---|---|---|---|---|---|
| | $D_2$ | $D_3$ | $D_4$ | $D_2/D_3$ | $D_2/D_4$ |
| Clozapine (Control compound) | 260 | 230 | 51 | 1.1 | 5.1 |
| Example 7 | 72 | 1.5 | 1.1 | 48 | 65 |
| Example 19 | 350 | 4.0 | 2.6 | 88 | 135 |
| Example 30 | 34 | 3.5 | 1.8 | 9.7 | 19 |

In this receptor binding test, the compounds of the present invention showed high affinity for $D_3$ receptor and/or $D_4$ receptor and excellent $D_3$ receptor and/or $D_4$ receptor selectivity against $D_2$ receptor in comparison with a known antipsychotic agent (clozapine).

On the other hand, other typically known dopamine receptor blocking agent showed affinity for $D_2$, $D_3$ and $D_4$ receptors at various ratios, but none of them showed selective affinity for $D_3$ and/or $D_4$ receptor.

2) Antagonism test on apomorphine-induced climbing behavior

In order to evaluate antipsychotic action of the compound of the present invention, antagonism of the compound of the present invention and clozapine against apomorphine-induced climbing behavior was measured. Each test compound was administered to ICR mice (body weight, around 35 g; Japan SLC) by subcutaneous injection and, after 15 minutes, apomorphine (2 mg/kg) was subcutaneously injected. After 10 minutes of the final injection, climbing behavior of the mice was measured during 30 minutes to calculate $ED_{50}$ value.

As a result, the compound of the present invention showed potent antagonism against apomorphine-induced climbing behavior (Table 3).

TABLE 3

| Compound | $ED_{50}$ (mg/kg, SC adininistration) |
|---|---|
| Clozapine (Control compound) | 6.8 |
| Example 30 | 1.8 |

In consequence, usefulness of the compound of the present invention as an antipsychotic agent can be expected.

When the compound represented by the general formula (I), a non-toxic salt thereof, a stereoisomer thereof or a hydrate or solvate thereof is used for the above purpose, it may be administered orally or parenterally.

The dose may vary depending on the age, body weight, symptoms, therapeutic effect, administration method, treating period and the like, but, in general, it may be administered orally within a range of from 0.1 mg to 100 mg, preferably from 1 mg to 50 mg, per day per adult, by dividing the daily dose into one to several doses per day, or parenterally within a range of from 0.1 mg to 100 mg per day per adult, by dividing the daily dose into one to several doses per day or by continuously administering the daily dose by intravenous injection for 1 to 24 hours a day. Since the dose varies depending on various conditions, a dose smaller than the above range may be enough in some cases.

Tablets, powders, granules and the like may be used as the solid composition for oral administration use of the present invention. In such a solid composition, one or more active substances are mixed with at least one inert diluent such as lactose, mannitol, glucose, hydroxypropylcellulose, micro-crystalline cellulose, starch, polyvinyl pyrrolidone, magnesium metasilicate aluminate or the like. In accordance with the conventionally used method, the composition may contain additive agents other than the inert diluent, such as lubricating agents (e.g., magnesium stearate), disintegrating agents (e.g., calcium cellulose glycolate), stabilizing agents (e.g., galactose), and solubilizing aids (e.g., glutamic acid, aspartic acid). As occasion demands, tablets or pills may be coated with gastric or enteric coating films such as of sucrose, gelatin, hydroxypropylcellulose, hydroxypropylmethylcellulose phthalate and the like.

Examples of liquid composition for use in oral administration include pharmaceutically acceptable emulsions, solutions, suspensions, syrups, elixirs and the like which contain a generally used inert diluent such as purified water, ethanol or the like. In addition to the inert diluent, this composition may also contain auxiliary agents such as a moistening agent and a suspending agent, as well as a sweetening agent, a flavoring agent, an aroma, an antiseptic agent and the like.

Injections for use in parenteral administration include aseptic aqueous or non-aqueous solutions, suspensions and emulsions. Examples of the aqueous solutions and suspensions include distilled water for injection use and physiological saline. Examples of the non-aqueous solutions and suspensions include propylene glycol, polyethylene glycol, plant oil such as olive oil, alcohol such as ethanol, Polysorbate 80 (trade name, a nonionic surface active agent, polyoxyethylene sorbitan alkyl ester) and the like. Such a composition may also contain auxiliary agents such as an antiseptic agent, a moistening agent, an emulsifying agent, a dispersing agent, a stabilizing agent (e.g., lactose), a solubilizing aid (e.g., glutamic acid or aspartic acid) and the like. Sterilization of these compositions may be effected by passing them through a bacterial filter, formulating a germicide or light irradiation. Alternatively, a corresponding aseptic solid composition may be produced which is used by dissolving in aseptic water or an aseptic solvent for injection use prior to its use.

BEST MODE OF CARRYING OUT THE INVENTION

Examples of the present invention are given below by way of illustration and not by way of limitation. First, examples of the production of starting compounds to be used in the Examples are described as Reference Examples.

REFERENCE EXAMPLE 1

A 1.00 g portion of bicyclo[3.3.1]nonan-9-one and 1.35 g of (3S)-(−)-3-(tert-butoxycarbonylamino)pyrrolidine were dissolved in 50 ml of methanol, and the solution was mixed with 0.10 g of 10% palladium-carbon powder to carry out 2 hours of catalytic reduction at room temperature in an atmosphere of hydrogen. The reaction solution was filtered, and the resulting filtrate was concentrated under a reduced pressure and then purified by column chromatography (chloroform:methanol=10:1) to give 2.34 g of an intermediate, i.e., (3S)-1-(bicyclo[3.3.1]non-9-yl)-3-(tert-butoxycarbonylamino)pyrrolidine, in the form of a oily material. This was dissolved in 4N hydrochloric acid-ethyl acetate solution, followed by stirring for 30 minutes. A 30 ml portion of ether was added to the resulting reaction solution, and the thus formed crystals were collected by filtration and dried under a reduced pressure to give 1.80 g of (3S)-3-amino-1-(bicyclo[3.3.1]non-9-yl)pyrrolidine dihydrochloride as white crystals.

Mass spectrometry data (m/z) FAB-MS: 209 (M$^+$+1) Nuclear magnetic resonance spectrum (DMSO-d$_6$, TMS internal standard) δ: 1.49–1.58 (4H, m), 1.72–1.84 (6H, m), 2.55 (1H, m), 3.17–3.22 (2H, m), 3.31 (1H, m), 3.51–3.64 (2H, m), 3.74–3.87 (1H, m), 4.02–4.10 (1H, m), 8.80 (2H, brs), 10.28 (1H, brs), 10.73 (1H, brs)

REFERENCE EXAMPLE 2

A 2.00 g portion of 2-methoxy-4-methylbenzoic acid was dissolved in 10 ml of sulfuric acid. With stirring at 0° C., 0.88 ml of concentrated nitric acid was added thereto dropwise. After 4 hours of stirring at room temperature, and ice water was added. The thus formed crystals were collected by filtration, dried under a reduced pressure and then purified by column chromatography (chloroform:methanol= 30:1) to give 1.32 g of 2-methoxy-4-methyl-5-nitrobenzoic acid as yellow crystals.

Mass spectrometry data (m/z) EI-MS: 211 (M$^+$) Nuclear magnetic resonance spectrum (CDCl$_3$, TMS internal standard) δ: 2.72 (3H, s), 4.13 (3H, s), 6.95 (1H, s), 8.83 (1H, s)

REFERENCE EXAMPLE 3

In a stream of argon, 3.08 g of 4-amino-5-chloro-2-methoxybenzoic acid and 1.00 g of cyclohexanone were added to 30 ml of acetic acid at room temperature, 4.30 g of sodium triacetoxyborohydride was added in small portions to the above solution, and then the resulting mixture was stirred for 1 hour. After completion of the reaction, the solvent was evaporated and the resulting residue was mixed with water, extracted with chloroform and then washed with saturated brine. After drying over anhydrous sodium sulfate, the solvent was evaporated under a reduced pressure and the resulting residue was purified by silica gel column chromatography (chloroform:methanol=100:1–50:1) to give 0.37 g of 5-chloro-4-cyclohexylamino-2-methoxybenzoic acid.

Mass spectrometry data (m/z) FAB-MS: 284 (M$^+$+1) Nuclear magnetic resonance spectrum (CDCl$_3$, TMS internal standard) δ: 1.00–2.30 (10H, m), 3.15–3.60 (1H, m), 4.03 (3H, s), 4.70–5.00 (1H, m), 6.14 (1H, s), 8.03 (1H, s), 9.80–10.80 (1H, brs)

REFERENCE EXAMPLE 4

In the similar manner as described in Reference Example 3, 0.56 g of 5-chloro-2-methoxy-4-propylaminobenzoic acid was obtained from 0.36 ml of propanal.

Mass spectrometry data (m/z) FAB-MS: 244 (M$^+$+1) Nuclear magnetic resonance spectrum (DMSO-d$_6$, TMS internal standard) δ: 0.92 (3H, t, J=7.5 Hz), 1.58–1.64 (2H, m), 3.21 (2H, m), 3.81 (3H, s), 6.01 (1H, t, J=5.5 Hz), 6.24 (1H, s), 7.62 (1H, s), 11.87 (1H, brs)

REFERENCE EXAMPLE 5

In the same manner as described in Reference Example 3, 0.61 g of 5-chloro-4-cyclopropylmethylamino-2-methoxybenzoic acid was obtained from 0.37 ml of cyclopropylaldehyde.

Mass spectrometry data (m/z) FAB-MS: 256 (M$^+$+1) Nuclear magnetic resonance spectrum (DMSO-d$_6$, TMS internal standard) δ: 0.26–0.29 (2H, m), 0.46–0.51 (2H, m), 1.07–1.90 (1H, m), 3.12–3.15 (2H, m), 3.82 (3H, s), 6.00 (1H, t, J=5.5 Hz), 6.31 (1H, s), 7.63 (1H, s), 11.86 (1H, s)

REFERENCE EXAMPLE 6

In the similar manner as described in Reference Example 3, 0.61 g of 5-chloro-2-methoxy-4-neopentylaminobenzoic acid was obtained from 0.98 ml of pivalaldehyde.

Mass spectrometry data (m/z) FAB-MS: 272 (M$^+$+1) Nuclear magnetic resonance spectrum (DMSO-d$_6$, TMS internal standard) δ: 0.95 (9H, s), 3.10–3.12 (2H, m), 3.81 (3H, s), 5.57 (1H, t, J=6.5 Hz), 6.37 (1H, s), 7.63 (1H, s), 11.87 (1H, s)

REFERENCE EXAMPLE 7

(1) In a stream of argon, 1.50 g of 4-chloro-2-methoxybenzoic acid was added to 10 ml of sulfuric acid under ice-cooling, and 0.85 g of potassium nitrate was added to the solution in small portions, followed by 2 hours of stirring. After completion of the reaction, the reaction solution was poured on crushed ice, and the thus precipitated product of interest was collected by filtration, washed with methanol and then dried under a reduced pressure to give 1.74 g of 4-chloro-2-methoxy-5-nitrobenzoic acid.

Mass spectrometry data (m/z) EI-MS: 231 (M$^+$) Nuclear magnetic resonance spectrum (DMSO-d$_6$, TMS internal standard) δ: 3.98 (3H, s), 7.50 (1H, s), 8.40 (1H, s), 12.50–13.50 (1H, brs)

(2) In a stream of argon, 0.45 g of sodium methanethiolate was added to 5 ml of dimethyl sulfoxide at room temperature, and 0.50 g of 4-chloro-5-nitro-2-methoxybenzoic acid was added in small portions, followed by 2 hours of stirring. After completion of the reaction, the reaction solution was poured into 1N hydrochloric acid aqueous solution, and the thus precipitated product of interest was collected by filtration, washed with water and then dried under a reduced pressure to give 0.45 g of 2-methoxy-4-methylthio-5-nitrobenzoic acid.

Mass spectrometry data (m/z) EI-MS: 243 (M$^+$) Nuclear magnetic resonance spectrum (DMSO-d$_6$, TMS internal standard) δ: 2.63 (3H, s), 4.05 (3H, s), 6.97 (1H, s), 8.60 (1H, s), 12.60–13.50 (1H, brs)

REFERENCE EXAMPLE 8

In a stream of argon, 0.30 g of metallic sodium was added to 5 ml of methanol under ice-cooling, the mixture was stirred at room temperature for a while and then 1.00 g of 4-chloro-2-methoxy-5-nitrobenzoic acid was added to the resulting solution in small portions, followed by stirring at 80° C. for 8 hours. After completion of the reaction, the reaction solution was poured into 1N hydrochloric acid aqueous solution, and the thus precipitated product of interest was collected by filtration, washed with water and then dried under a reduced pressure to give 0.80 g of 2,4-dimethoxy-5-nitrobenzoic acid.

Mass spectrometry data (m/z) EI-MS: 227 (M$^+$) Nuclear magnetic resonance spectrum (DMSO-d$_6$, TMS internal standard) δ: 4.00 (3H, s), 4.05 (3H, s), 6.88 (1H, s), 8.38 (1H, s), 12.70–13.30 (1H, brs)

(Alternative method) A 2.00 g portion of 2,4-dimethoxybenzoic acid was dissolved in 30 ml of sulfuric acid, and 0.49 ml of concentrated nitric acid was added under ice-cooling. After 3 hours of stirring at room temperature, this was poured into 100 g of ice water, and the thus formed crystals were collected by filtration, washed with water-methanol and then dried under a reduced pressure to give 1.41 g of 2,4-dimethoxy-5-nitrobenzoic acid. The physicochemical properties were identical to those of the compound obtained by the former method.

REFERENCE EXAMPLE 9

A 0.50 g portion of 2-methoxy-4-methylthio-5-nitrobenzoic acid was suspended in 5 ml of acetic acid, and 0.77 ml of 30% hydrogen peroxide aqueous solution was added thereto, followed by 12 hours of stirring. After completion of the reaction, the reaction solution was poured on crushed ice, and the thus precipitated product of interest was collected by filtration, washed with water and then dried under a reduced pressure to give 0.35 g of 4-methylsulfinyl-2-methoxy-5-nitrobenzoic acid.

Mass spectrometry data (m/z) EI-MS: 259 (M$^+$) Nuclear magnetic resonance spectrum (DMSO-d$_6$, TMS internal standard) δ: 2.91 (3H, s), 4.08 (3H, s), 7.78 (1H, s), 8.55 (1H, s)

REFERENCE EXAMPLE 10

A 1.00 g portion of 4-chloro-2-methoxy-5-nitrobenzoic acid and 0.52 g of sodium hydroxide were dissolved in 20 ml of 40% methylamine methanol solution, followed by stirring at room temperature for 12 hours. After completion of the reaction, the reaction solution was poured on crushed ice and adjusted to pH 4 with 6N hydrochloric acid aqueous solution. The thus precipitated product of interest was collected by filtration, washed with water and dried under a reduced pressure and then the resulting crude product was purified by silica gel column chromatography (chloroform:methanol=20:1) to give 0.30 g of 2-methoxy-4-methylamino-5-nitrobenzoic acid.

Mass spectrometry data (m/z) EI-MS: 226 (M$^+$) Nuclear magnetic resonance spectrum (DMSO-d$_6$, TMS internal standard) δ: 3.02 (3H, d, J=4.5 Hz), 3.91 (3H, s), 6.24 (1H, s), 8.52 (1H, s)

REFERENCE EXAMPLE 11

In a stream of argon, 0.49 ml of 1-propanol was added to 5 ml of dimethylformamide, and 0.24 g of sodium hydride was added, followed by a short period of stirring at room temperature. To the resulting solution was added 0.50 g of 4-chloro-2-methoxy-5-nitrobenzoic acid in small portions, followed by 2 hours of stirring. After completion of the reaction, the reaction solution was poured into 1N hydrochloric acid aqueous solution, the thus precipitated product of interest was collected by filtration, washed with water and dried under a reduced pressure. The resulting crude product was purified by silica gel column chromatography (chloroform:methanol=100:1–10:1) to give 0.07 g of 2,4-dipropoxy-5-nitrobenzoic acid.

Mass spectrometry data (m/z) EI-MS: 283 (M$^+$) Nuclear magnetic resonance spectrum (DMSO-d$_6$, TMS internal standard) δ: 0.98–1.04 (6H, m), 1.73–1.82 (4H, m), 4.16 (2H, t, J=6.5 Hz), 4.23 (2H, t, J=6.5 Hz), 6.84 (1H, s), 8.35 (1H, s), 12.80 (1H, brs)

REFERENCE EXAMPLE 12

(1) A 7.00 g portion of 2,4-dimethoxy-5-nitrobenzoic acid was dissolved in 2-butanone, and 9.90 g of potassium carbonate and 3.6 ml of dimethyl sulfate were added, followed by 3 hours of heating under reflux. After completion of the reaction, the reaction solution was poured into 1N hydrochloric acid aqueous solution, and the thus precipitated product of interest was collected by filtration, washed with water and then dried under a reduced pressure to give 5.45 g of methyl 2,4-dimethoxy-5-nitrobenzoate.

Mass spectrometry data (m/z) EI-MS: 241 (M$^+$) Nuclear magnetic resonance spectrum (DMSO-d$_6$, TMS internal standard) δ: 3.79 (3H, s), 4.00 (3H, s), 4.06 (3H, s), 6.90 (1H, s), 8.38 (1H, s)

(2) A 4.00 g portion of methyl 2,4-dimethoxy-5-nitrobenzoate was dissolved in 200 ml of tetrahydrofuran, and 0.40 g of 10% palladium-carbon was added, followed by stirring for 12 hours at room temperature under normal pressure in an atmosphere of hydrogen. After removing insoluble matter by filtration, the solvent was evaporated under a reduced pressure to give 3.6 g of methyl 5-amino-2,4-dimethoxybenzoate.

Mass spectrometry data (m/z) EI-MS: 211 (M$^+$) Nuclear magnetic resonance spectrum (DMSO-d$_6$, TMS internal standard) δ: 3.72 (3H, s), 3.75 (3H, s), 3.86 (3H, s), 4.47–4.49 (2H, brs), 6.62 (1H, s), 7.08 (1H, s)

(3) A 0.65 g portion of methyl 5-amino-2,4-dimethoxybenzoate was dissolved in a mixture solvent of 1.5 ml of water and 10 ml of acetone, and 1.3 ml of concentrated hydrochloric acid was added thereto, followed by dropwise addition of 0.23 g of sodium nitrite dissolved in 1 ml of water under ice-cooling and subsequent stirring for a while. Next, 0.35 g of cuprous chloride was added and the mixture was warmed up to room temperature. After completion of the reaction, insoluble matter was filtered and the resulting residue was mixed with water, extracted with ethyl acetate and then washed with water and saturated brine. After drying over anhydrous sodium sulfate, the solvent was evaporated under a reduced pressure and the resulting residue was purified by silica gel column chromatography (chloroform:methanol=500:1–40:1) to give 0.56 g of methyl 5-chloro-2,4-dimethoxybenzoate.

Mass spectrometry data (m/z) EI-MS: 230 (M$^+$) Nuclear magnetic resonance spectrum (DMSO-d$_6$, TMS internal standard) δ: 3.75 (3H, s), 3.89 (3H, s), 3.97 (3H, s), 6.83 (1H, s), 7.72 (1H, s)

(4) A 0.56 g portion of methyl 5-chloro-2,4-dimethoxybenzoate was dissolved in 5 ml of tetrahydrofuran, and 10 ml of 2N sodium hydroxide aqueous solution was added, followed by 4 hours of heating under reflux. After completion of the reaction, the reaction solution was poured into 1N hydrochloric acid aqueous solution, and the thus precipitated product of interest was collected by filtration, washed with water and then dried under a reduced pressure to give 0.45 g of 5-chloro-2,4-dimethoxybenzoic acid.

Mass spectrometry data (m/z) EI-MS: 216 (M$^+$) Nuclear magnetic resonance spectrum (DMSO-d$_6$, TMS internal standard) δ: 3.89 (3H, s), 3.96 (3H, s), 6.82 (1H, s), 7.71 (1H, s), 12.40–12.60 (1H, brs)

REFERENCE EXAMPLE 13

(1) A 1.50 g portion of methyl 2,4-dihydroxybenzoate was dissolved in 30 ml of acetone, and 3.10 g of potassium carbonate and 1.7 ml of isopropyl iodide were added, followed by 48 hours of heating under reflux. After completion of the reaction, the reaction solution was poured into 1N hydrochloric acid aqueous solution, extracted with chloroform and dried over anhydrous sodium sulfate and then the solvent was evaporated under a reduced pressure. The resulting residue was purified by silica gel column chromatography (hexane:ethyl acetate=10:1–2:1) to give 1.60 g of methyl 2-hydroxy-4-isopropoxybenzoate.

Mass spectrometry data (m/z) EI-MS: 210 (M$^+$) Nuclear magnetic resonance spectrum (CDCl$_3$, TMS internal standard) δ: 1.42 (6H, d, J=7.0 Hz), 3.90 (3H, s), 4.43–4.72 (1H, m), 6.31–6.44 (2H, m), 7.65–7.77 (1H, m), 10.91 (1H, s)

(2) A 1.60 g portion of methyl 2-hydroxy-4-isopropoxybenzoate was dissolved in 30 ml of 2-butanone, 1.60 g of potassium carbonate and 1.1 ml of dimethyl sulfate were added, followed by 12 hours of heating under reflux.

After completion of the reaction, the solvent was evaporated, the resulting residue was suspended in chloroform, insoluble matter was removed by filtration through celite, and the solvent was again evaporated. The resulting residue was purified by silica gel column chromatography (hexane:ethyl acetate=10:1–2:1) to give 1.70 g of methyl 4-isopropoxy-2-methoxybenzoate.

Mass spectrometry data (m/z) EI-MS: 224 ($M^+$) Nuclear magnetic resonance spectrum ($CDCl_3$, TMS internal standard) δ: 1.36 (6H, d, J=6.0 Hz), 3.85 (3H, s), 3.87 (3H, s), 4.46–4.76 (1H, m), 6.38–6.54 (2H, m), 7.76–7.88 (1H, m)

(3) A 3.20 g portion of methyl 4-isopropoxy-2-methoxybenzoate was dissolved in 20 ml of tetrahydrofuran, and 30 ml of 2N sodium hydroxide aqueous solution was added, followed by 2 hours of heating under reflux. After completion of the reaction, the reaction solution was poured into 1N hydrochloric acid aqueous solution, extracted with chloroform and dried over anhydrous sodium sulfate. Then, the solvent was evaporated under a reduced pressure to give 2.60 g of 4-isopropoxy-2-methoxybenzoic acid.

Mass spectrometry data (m/z) EI-MS: 210 ($M^+$) Nuclear magnetic resonance spectrum (DMSO-$d_6$, TMS internal standard) δ: 1.27 (6H, d, J=6.0 Hz), 3.78 (3H, s), 4.50–4.90 (1H, m), 6.48–6.58 (2H, m), 7.62–7.73 (1H, m), 12.00–12.20 (1H, brs)

(4) A 1.61 g portion of 4-isopropoxy-2-methoxybenzoic acid was dissolved in 20 ml of acetic anhydride, 0.38 ml of concentrated nitric acid and a small amount of acetic acid were added, followed by stirring at room temperature for 2 hours. After completion of the reaction, the reaction solution was poured on crushed ice, extracted with chloroform and then dried over anhydrous sodium sulfate. After evaporation of the solvent under a reduced pressure, the resulting residue was dissolved in 5 ml of tetrahydrofuran and 5 ml of 1N sodium hydroxide aqueous solution, followed by stirring for 1 hour. The reaction solution was poured into 1N hydrochloric acid aqueous solution, extracted with chloroform and dried over anhydrous sodium sulfate. The solvent was evaporated under a reduced pressure and the resulting residue was purified by silica gel column chromatography (chloroform:methanol=100:1–10:1) to give 0.43 g of 4-isopropoxy-2-methoxy-5-nitrobenzoic acid.

Mass spectrometry data (m/z) EI-MS: 255 ($M^+$) Nuclear magnetic resonance spectrum (DMSO-$d_6$, TMS internal standard) δ: 1.35 (6H, d, J=6.0 Hz), 3.96 (3H, s), 4.80–5.20 (1H, m), 6.87 (1H, s), 8.29 (1H, s)

REFERENCE EXAMPLE 14

(1) In the similar manner as described in Reference Example 13 (1), 1.50 g of methyl 2-hydroxy-4-propoxybenzoate was obtained from 1.7 ml of propyl iodide.

Mass spectrometry data (m/z) EI-MS: 210 ($M^+$) Nuclear magnetic resonance spectrum ($CDCl_3$, TMS internal standard) δ: 1.03 (3H, t, J=7.0 Hz), 1.77–1.84 (2H, m), 3.91 (3H, s), 3.91–3.96 (2H, m), 6.40–6.44 (2H, m), 7.70–7.74 (1H, m), 10.93 (1H, s)

(2) In the similar manner as described in Reference Example 13 (2), 1.60 g of methyl 2-methoxy-4-propoxybenzoate was obtained from 1.50 g of methyl 2-hydroxy-4-propoxybenzoate.

Mass spectrometry data (m/z) EI-MS: 224 ($M^+$) Nuclear magnetic resonance spectrum ($CDCl_3$, TMS internal standard) δ: 1.05 (3H, t, J=7.5 Hz), 1.65–1.94 (2H, m), 3.81 (3H, s), 3.85 (3H, s), 3.81–4.04 (2H, m), 6.40–6.54 (2Hm) 7.77–7.89 (1H, m)

(3) In the similar manner as described in Reference Example 13 (3), 1.40 g of 2-methoxy-4-propoxybenzoic acid was obtained from 1.60 g of methyl 2-methoxy-4-propoxybenzoate.

Mass spectrometry data (m/z) EI-MS: 210 ($M^+$) Nuclear magnetic resonance spectrum (DMSO-$d_6$, TMS internal standard) δ: 0.98 (3H, t, J=7.5 Hz), 1.68–1.79 (2H, m), 3.81 (3H, s), 4.00 (2H, t, J=7.0 Hz), 6.53–6.61 (2H, m), 7.69 (2H, d, J=8.5 Hz), 12.11 (1H, s)

(4) In the similar manner as described in Reference Example 13 (4), 3.20 g of 2-methoxy-5-nitro-4-propoxybenzoic acid was obtained from 3.00 g of 2-methoxy-4-propoxybenzoic acid.

Mass spectrometry data (m/z) EI-MS: 255 ($M^+$) Nuclear magnetic resonance spectrum (DMSO-$d_6$, TMS internal standard) δ: 1.02 (3H, t, J=7.5 Hz), 1.76–1.82 (2H, m), 3.97 (3H, s), 4.25 (2H, t, J=6.0 Hz), 6.86 (1H, s), 8.36 (1H, s), 12.83–12.92 (1H, brs)

REFERENCE EXAMPLE 15

(1) A 1.00 g portion of methyl 5-amino-2,4-dimethoxybenzoate was dissolved in 5 ml of water, 0.50 ml of concentrated sulfuric acid was added and then 356 mg of sodium nitrite dissolved in 2 ml of water was added dropwise under ice-cooling, followed by a short period of stirring. Separately, 1.00 g of cuprous cyanide was dissolved in 4 ml of water and, with ice-cooling, 2.00 g of sodium cyanide dissolved in 4 ml of water was added dropwise thereto, followed by 1 hour of stirring. This was mixed with the previously prepared solution and heated at 80° C. to effect the reaction, the resulting reaction solution was mixed with water, extracted with chloroform and dried over anhydrous sodium sulfate. The solvent was evaporated under a reduced pressure and then the resulting residue was purified by silica gel column chromatography (hexane:ethyl acetate= 6:1 to chloroform:methanol=50:1) to give 0.65 g of methyl 5-cyano-2,4-dimethoxybenzoate.

Mass spectrometry data (m/z) EI-MS: 221 ($M^+$) Nuclear magnetic resonance spectrum (DMSO-$d_6$, TMS internal standard) δ: 3.77 (3H, s), 3.97 (3H, s), 4.03 (3H, s), 6.86 (1H, s), 8.02 (1H, s)

(2) A 0.80 g portion of methyl 5-cyano-2,4-dimethoxybenzoate was dissolved in 8 ml of acetonitrile and 5 ml of water, and 7 ml of 2N sodium hydroxide aqueous solution was added, followed by stirring at room temperature for 6 hours. After completion of the reaction, the reaction solution was poured into 2N hydrochloric acid aqueous solution, extracted with chloroform and dried over anhydrous sodium sulfate. The solvent was evaporated under a reduced pressure to give 0.65 g of 5-cyano-2,4-dimethoxybenzoic acid.

Mass spectrometry data (m/z) EI-MS: 207 ($M^+$) Nuclear magnetic resonance spectrum (DMSO-$d_6$, TMS internal standard) δ: 3.96 (3H, s), 4.02 (3H, s), 6.84 (1H, s), 8.00 (1H, s), 12.73 (1H, s)

REFERENCE EXAMPLE 16

(1) In the similar manner as described in Reference Example 13 (1), 3.00 g of methyl 4-cyclopropylmethyloxy-2-hydroxybenzoate was obtained from 5.00 g of cyclopropylmethyl bromide.

Mass spectrometry data (m/z) EI-MS: 222 ($M^+$) Nuclear magnetic resonance spectrum ($CDCl_3$, TMS internal standard) δ: 0.32–0.40 (2H, m), 0.59–0.80 (2H, m), 1.10–1.54 (1H, m), 3.77–3.91 (2H, m), 3.91 (3H, s), 6.40–6.49 (2H, m), 7.66–7.79 (1H, m), 10.93 (1H, s)

(2) A 3.00 g portion of methyl 4-cyclopropylmethyloxy-2-hydroxybenzoate was dissolved in 70 ml of 2-butanone, and 2.80 g of potassium carbonate and 1.9 ml of dimethyl sulfate were added, followed by 12 hours of heating under reflux. After completion of the reaction, the solvent was evaporated, the resulting residue was suspended in chloroform, and insoluble matter was removed by celite filtration. The solvent was again evaporated, and then the thus obtained residue was dissolved in 20 ml of tetrahydrofuran, mixed with 30 ml of 2N sodium hydroxide aqueous solution and subjected to 3 hours of heating under reflux. After completion of the reaction, the reaction solution was poured into 1N hydrochloric acid aqueous solution, and the thus precipitated product of interest was collected by filtration, washed with water and then dried under a reduced pressure to give 2.74 g of 4-cyclopropylmethyloxy-2-methoxybenzoic acid.

Mass spectrometry data (m/z) EI-MS: 222 (M⁺) Nuclear magnetic resonance spectrum (DMSO-$d_6$, TMS internal standard) δ: 0.30–0.36 (2H, m), 0.55–0.61 (2H, m), 1.21–1.25 (1H, m), 3.80 (3H, s), 3.89 (2H, d, J=7.0 Hz), 6.54 (1H, dd, J=2.0, 8.5 Hz), 6.61 (1H, d, J=2.0 Hz), 7.68 (1H, d, J=8.5 Hz), 12.10 (1H, s)

(3) In the similar manner as described in Reference Example 13 (4), 3.00 g of 4-cyclopropylmethyloxy-2-methoxy-5-nitrobenzoic acid was obtained from 2.65 g of 4-cyclopropylmethyloxy-2-methoxybenzoic acid.

Mass spectrometry data (m/z) EI-MS: 267 (M⁺) Nuclear magnetic resonance spectrum (DMSO-$d_6$, TMS internal standard) 0.37–0.42 (2H, m), 0.60–0.65 (2H, m), 1.26–1.31 (1H, m), 3.96 (3H, s), 4.17 (2H, d, J=6.5 Hz), 6.83 (1H, s), 8.35 (1H, s), 12.83–12.87 (1H, s)

REFERENCE EXAMPLE 17

(1) In the similar manner as described in Reference Example 13 (1), 2.74 g of methyl 4-benzyloxy-2-hydroxybenzoate was obtained from 3.2 ml of benzyl bromide.

Mass spectrometry data (m/z) EI-MS: 258 (M⁺) Nuclear magnetic resonance spectrum (CDCl₃, TMS internal standard) δ: 3.90 (3H, s), 5.07 (2H, s), 6.48–6.54 (2H, m), 7.32–7.43 (5H, m), 7.74 (1H, d, J=8.75 Hz), 10.96 (1H, s)

(2) In the similar manner as described in Reference Example 16 (2), 2.66 g of 4-benzyloxy-2-methoxybenzoic acid was obtained from 2.74 g of methyl 4-benzyloxy-2-hydroxybenzoate.

Mass spectrometry data (m/z) EI-MS: 258 (M⁺) Nuclear magnetic resonance spectrum (CDCl₃, TMS internal standard) δ: 4.02 (3H, s), 5.13 (2H, s), 6.62 (1H, d, J=2.5 Hz), 6.73 (1H, dd, J=8.75, 2.5 Hz), 7.33–7.44 (5H, m), 8.14 (1H, d, J=8.75 Hz), 10.45–10.49 (1H, brs)

(3) In the similar manner as described in Reference Example 13 (4), 0.45 g of 4-benzyloxy-2-methoxy-5-nitrobenzoic acid was obtained from 1.00 g of 4-benzyloxy-2-methoxybenzoic acid.

Mass spectrometry data (m/z) EI-MS: 303 (M⁺) Nuclear magnetic resonance spectrum (DMSO-$d_6$, TMS internal standard) δ: 3.98 (3H, s), 5.46 (2H, s), 7.02 (1H, s), 7.34–7.55 (5H, m), 8.39 (1H, s), 12.90 (1H, s)

REFERENCE EXAMPLE 18

(1) A 3.00 g portion of methyl 2,4-dihydroxybenzoate was dissolved in 30 ml of tetrahydrofuran, and 2 ml of cyclohexanol, 9.00 g of triphenylphosphine and 7.38 ml of diisopropyl azodicarboxylate were added, followed by stirring for 12 hours at room temperature. After completion of the reaction, the solvent was evaporated, the resulting residue was mixed with hexane-ethyl acetate, and insoluble matter was removed by filtration. Solvent of the filtrate was evaporated and the resulting residue was purified by silica gel column chromatography (hexane:ethyl acetate= 12:1–2:1) to give 1.70 g of methyl 4-cyclohexyloxy-2-hydroxybenzoate. Nuclear magnetic resonance spectrum (DMSO-$d_6$, TMS internal standard) δ: 1.10–2.10 (10H, m), 3.86 (3H, s), 4.40–4.48 (1H, m), 6.43–6.58 (2H, m), 7.63–7.75 (1H, m), 10.71 (1H, s)

(2) In the similar manner as described in Reference Example 16 (2), 1.70 g of 4-cyclohexyloxy-2-methoxybenzoic acid was obtained from 1.70 g of methyl 4-cyclohexyloxy-2-hydroxybenzoate.

Mass spectrometry data (m/z) EI-MS: 250 (M⁺) Nuclear magnetic resonance spectrum (CDCl₃, TMS internal standard) δ: 1.28–1.44 (3H, m), 1.53–1.63 (3H, m), 1.80–1.88 (2H, m), 1.98–2.05 (2H, m), 4.02 (3H, s), 4.32–4.39 (1H, m), 6.52 (1H, d, J=2.0 Hz), 6.61 (1H, dd, J=2.0, 9.0 Hz), 8.06 (1H, d, J=9.0 Hz)

(3) In the similar manner as described in Reference Example 13 (4), 1.48 g of 4-cyclohexyloxy-2-methoxy-5-nitrobenzoic acid was obtained from 1.60 g of 4-cyclohexyloxy-2-methoxybenzoic acid.

Mass spectrometry data (m/z) EI-MS: 295 (M⁺) Nuclear magnetic resonance spectrum (DMSO-$d_6$, TMS internal standard) δ: 1.27–1.90 (10H, m), 3.96 (3H, s), 4.87–4.93 (1H, m), 6.88 (1H, s), 8.33 (1H, s), 12.81–12.85 (1H, brs)

REFERENCE EXAMPLE 19

(1) A 1.00 g portion of norcamphor and 1.60 g of (3S)-3-(tert-butoxycarbonylamino)pyrrolidine were dissolved in 20 ml of methanol, and 0.20 g of 10% palladium-carbon powder was added, followed by stirring at room temperature for 12 hours in an atmosphere of hydrogen. The reaction solution was filtered, the thus obtained filtrate was concentrated under a reduced pressure. Then, the resulting residue was purified by silica gel column chromatography (chloroform:methanol=100:1–18:1) to give 2.27 g of (3S)-3-(tert-butoxycarbonylamino)-1-(8,9,10-trinorborn-2-yl) pyrrolidine.

Mass spectrometry data (m/z) EI-MS: 280 (M⁺) Nuclear magnetic resonance spectrum (DMSO-$d_6$, TMS internal standard) δ: 0.80–0.83 (1H, m), 1.12–1.28 (3H, m), 1.28–1.36 (2H, m), 1.37 (9H, s), 1.38–1.75 (3H, m), 1.76–1.80 (1H, m), 1.90–2.05 (1H, m), 2.05–2.25 (2H, m), 2.28–2.50 (2H, m), 2.60–2.70 (1H, m), 3.25–3.40 (1H, m), 3.75–3.90 (1H, m), 6.87–6.91 (1H, m)

(2) A 2.27 g portion of (3S)-3-(tert-butoxycarbonylamino)-1-(8,9,10-trinorborn-2-yl)pyrrolidine was dissolved in 20 ml of 4N hydrochloric acid-ethyl acetate solution, followed by 3 hours stirring. After evaporation of the solvent, the thus obtained product of interest, i.e., (3S)-3-amino-1-(8,9,10-trinorborn-2-yl)pyrrolidine dihydrochloride, was used in the next reaction without purification.

REFERENCE EXAMPLE 20

(1) In the similar manner as described in Reference Example 13 (3), 5-amino-2,4-dimethoxybenzoic acid was obtained from 0.50 g of methyl 5-amino-2,4-dimethoxybenzoate.

Mass spectrometry data (m/z) EI-MS: 197 (M⁺) Nuclear magnetic resonance spectrum (DMSO-$d_6$, TMS internal standard) δ: 3.77 (3H, s), 3.85 (3H, s), 6.61 (1H, s), 7.09 (1H, s)

REFERENCE EXAMPLE 21

(1) A 0.65 g portion of methyl 5-amino-2,4-dimethoxybenzoate was dissolved in 10 ml of acetone and 1.5 ml of water, 1.80 ml of 48% hydrobromic acid was added, and then 0.23 g of sodium nitrite dissolved in 1 ml of water was added dropwise under ice-cooling, followed by a short period of stirring. Next, 0.51 g of cuprous bromide was added, and the mixture was warmed to room temperature. After completion of the reaction, insoluble matter was filtered, and the resulting residue was mixed with water, extracted with chloroform and then dried over anhydrous sodium sulfate. By evaporating the solvent under a reduced pressure, methyl 5-bromo-2,4-dimethoxybenzoate was obtained.

Mass spectrometry data (m/z) EI-MS: 276 (M$^+$) Nuclear magnetic resonance spectrum (DMSO-d$_6$, TMS internal standard) δ: 3.75 (3H, s), 3.89 (3H, s), 3.96 (3H, s), 6.81 (1H, s), 7.86 (1H, s)

(2) In the similar manner as described in Reference Example 13 (3), 0.45 g of 5-bromo-2,4-dimethoxybenzoic acid was obtained from methyl 5-bromo-2,4-dimethoxybenzoate.

Mass spectrometry data (m/z) EI-MS: 260 (M$^+$) Nuclear magnetic resonance spectrum (DMSO-d$_6$, TMS internal standard) δ: 3.89 (3H, s), 3.96 (3H, s), 6.79 (1H, s), 7.86 (1H, s), 12.49 (1H, brs)

REFERENCE EXAMPLE 22

(1) In the similar manner as described in Reference Example 13 (4), 3.62 g of methyl 2-methoxy-5-nitro-4-propoxybenzoate was obtained from methyl 2-methoxy-4-propoxybenzoate.

Mass spectrometry data (m/z) EI-MS: 269 (M$^+$) Nuclear magnetic resonance spectrum (DMSO-d$_6$, TMS internal standard) δ: 1.02 (3H, t, J=7.5 Hz), 1.74–1.85 (2H, m), 3.79 (3H, s), 3.98 (3H, s), 4.26 (2H, t, J=6.0 Hz), 6.88 (1H, s), 8.37 (1H, s)

(2) In the similar manner as described in Reference Example 12 (2), 2.90 g of methyl 5-amino-2-methoxy-4-propoxybenzoate was obtained from 3.20 g of methyl 2-methoxy-5-nitro-4-propoxybenzoate.

Mass spectrometry data (m/z) EI-MS: 239 (M$^+$) Nuclear magnetic resonance spectrum (DMSO-d$_6$, TMS internal standard) δ: 1.00 (3H, t, J=7.5 Hz), 1.72–1.82 (2H, m), 3.71 (3H, s), 3.73 (3H, s), 4.01 (2H, t, J=6.5 Hz), 4.43–4.45 (1H, brs), 6.59 (1H, s), 7.07 (1H, s)

(3) In the similar manner as described in Reference Example 15 (1), 1.96 g of methyl 5-cyano-2-methoxy-4-propoxybenzoate was obtained from 2.90 g of methyl 5-amino-2-methoxy-4-propoxybenzoate.

Mass spectrometry data (m/z) EI-MS: 249 (M$^+$) Nuclear magnetic resonance spectrum (DMSO-d$_6$, TMS internal standard) δ: 1.02 (3H, t, J=7.5 Hz), 1.75–1.84 (2H, m), 3.76 (3H, s), 3.95 (3H, s), 4.22 (2H, t, J=6.5 Hz), 6.85 (1H, s), 8.02 (1H, s)

(4) In the similar manner as described in Reference Example 15 (2), 1.55 g of 5-cyano-2-methoxy-4-propoxybenzoic acid was obtained from 1.96 g of methyl 5-cyano-2-methoxy-4-propoxybenzoate.

Mass spectrometry data (m/z) EI-MS: 235 (M$^+$) Nuclear magnetic resonance spectrum (DMSO-d$_6$, TMS internal standard) δ: 1.02 (3H, t, J=7.5 Hz), 1.74–1.83 (2H, m), 3.94 (3H, s), 4.21 (2H, t, J=6.5 Hz), 6.82 (1H, s), 7.99 (1H, s), 12.71 (1H, brs)

REFERENCE EXAMPLE 23

(1) In the similar manner as described in Reference Example 19 (1), 1.90 g of (3S)-1-(2-adamantyl)-3-(tert-butoxycarbonylamino)pyrrolidine was obtained from 0.85 g of 2-adamantanone.

Mass spectrometry data (m/z) EI-MS: 320 (M$^+$) Nuclear magnetic resonance spectrum (CDCl$_3$, TMS internal standard) δ: 1.45 (9H, s), 1.55–1.63 (2H, m), 1.66–1.72 (5H, m), 1.75–1.85 (4H, m), 1.85–1.97 (2H, m), 2.00–2.15 (3H, m), 2.15–2.30 (2H, m), 2.55–2.60 (2H, m), 2.76–2.90 (1H, m), 4.05–4.12 (1H, m), 4.80–4.90 (1H, m)

(2) In the similar manner as described in Reference Example 19 (2), 1.29 g of (3S)-1-(2-adamantyl)-3-aminopyrrolidine dihydrochloride was obtained from 1.90 g of (3S)-1-(2-adamantyl)-3-(tert-butoxycarbonylamino) pyrrolidine.

Mass spectrometry data (m/z) EI-MS: 220 (M$^+$) Nuclear magnetic resonance spectrum (DMSO-d$_6$, TMS internal standard) δ: 1.60–1.75 (2H, m), 1.75–1.87 (4H, m), 1.80–2.00 (4H, m), 2.12–2.30 (2H, m), 2.30–2.58 (4H, m), 2.70–3.00 (1H, m), 3.22–3.45 (1H, m), 3.47–3.89 (2H, m), 3.89–4.11 (1H, m), 4.12–4.20 (1H, m), 9.02 (3H, brs), 10.40–10.90 (1H, brm)

REFERENCE EXAMPLE 24

(1) Under ice-cooling, 1.00 g of 2,4-dimethoxybenzoic acid was gradually added to 2 ml of chlorosulfonic acid, followed by stirring at room temperature for 12 hours. The reaction solution was poured on crushed ice, and the thus precipitated product of interest was collected by filtration, washed with water and then dried under a reduced pressure to give 1.03 g of 5-chlorosulfonyl-2,4-dimethoxybenzoic acid.

Mass spectrometry data (m/z) EI-MS: 280 (M$^+$) Nuclear magnetic resonance spectrum (DMSO-d$_6$, TMS internal standard) δ: 3.87 (3H, s), 3.88 (3H, s), 6.62 (1H, s), 8.14 (1H, s), 13.74–13.84 (1H, brs)

(2) A 1.00 g portion of 5-chlorosulfonyl-2,4-dimethoxybenzoic acid was added to 5 ml of saturated aqueous ammonia, followed by stirring at room temperature for 1 hour. Then, 6N hydrochloric acid aqueous solution was added to the reaction solution, and the thus precipitated product of interest was collected by filtration, washed with water and then dried under a reduced pressure to give 0.81 g of 5-aminosulfonyl-2,4-dimethoxybenzoic acid.

Mass spectrometry data (m/z) EI-MS: 261 (M$^+$) Nuclear magnetic resonance spectrum (DMSO-d$_6$, TMS internal standard) δ: 3.94 (3H, s), 4.00 (3H, s), 6.80 (1H, s), 7.04 (2H, s), 8.15 (1H, s), 12.20–12.80 (1H, brs)

REFERENCE EXAMPLE 25

(1) A 1.96 g portion of acetic anhydride was mixed with 0.89 ml of formic acid, followed by stirring at 50° C. for 2 hours. The resulting solution was mixed with 1.5 g of methyl 5-amino-2,4-dimethoxybenzoate dissolved in advance in 3 ml of tetrahydrofuran, followed by 6 hours stirring. After completion of the reaction, the thus precipitated product of interest was collected by filtration, washed with diethyl ether and then dried under a reduced pressure to give 1.62 g of methyl 2,4-dimethoxy-5-formylaminobenzoate.

Mass spectrometry data (m/z) EI-MS: 239 (M$^+$) Nuclear magnetic resonance spectrum (DMSO-d$_6$, TMS internal standard) δ: 3.74 (3H, s), 3.86 (3H, s), 3.95 (3H, s), 6.78 (1H, s), 8.24 (1H, d, J=1.5 Hz), 8.50 (1H, s), 9.57–9.59 (1H, brm)

(2) A 1.60 g portion of methyl 2,4-dimethoxy-5-formylaminobenzoate was dissolved in 20 ml of tetrahydrofuran, and 1.7 ml of borane dimethylsulfide complex was added under ice-cooling, followed by 2 hours of stirring at 60° C. Then, 3 ml of methanol and 4 ml of concentrated hydrochloric acid were added, followed by stirring at 75° C. for a while and then spontaneously cooled. The thus precipitated product of interest was collected by filtration, washed with tetrahydrofuran and then dried under a reduced pressure to give 1.08 g of methyl 2,4-dimethoxy-5-methylaminobenzoate.

Mass spectrometry data (m/z) EI-MS: 225 (M$^+$) Nuclear magnetic resonance spectrum (DMSO-$d_6$, TMS internal standard) δ: 2.81 (3H, s), 3.77 (3H, s), 3.91 (3H, s), 4.02 (3H, s), 6.90 (1H, s), 7.88 (1H, s), 10.40–11.00 (1H, brs)

(3) In the similar manner as described in Reference Example 13 (3), 2,4-dimethoxy-5-methylaminobenzoic acid was obtained from 1.08 g of methyl 2,4-dimethoxy-5-methylaminobenzoate, which was used in the next reaction without purification.

REFERENCE EXAMPLE 26

(1) To 20 g of crushed ice were added 3.7 ml of concentrated sulfuric acid and 1.90 g of 5-chlorosulfonyl- 2,4-dimethoxybenzoic acid. Under ice-cooling, 2.40 g of zinc powder was added, and the mixture was then heated under reflux. After completion of the reaction, the reaction solution was diluted with ethyl acetate and insoluble matter was removed by celite filtration. The thus obtained filtrate was extracted with ethyl acetate, washed with water and saturated brine and then dried over anhydrous sodium sulfate. The solvent was evaporated under a reduced pressure and the resulting residue was washed with diethyl ether to give 0.74 g of 2,4-dimethoxy-5-mercaptobenzoic acid.

Mass spectrometry data (m/z) EI-MS: 214 (M$^+$) Nuclear magnetic resonance spectrum (CDCl$_3$, TMS internal standard) δ: 3.62 (1H, s), 3.99 (3H, s), 4.07 (3H, s), 6.50 (1H, s), 8.07 (1H, s), 10.15–10.70 (1H, brs)

(2) A 0.74 g portion of 2,4-dimethoxy-5-mercaptobenzoic acid was dissolved in 10 ml of dimethylformamide, and 0.56 g of potassium carbonate and 0.24 ml of methyl iodide were added, followed by stirring at room temperature for 12 hours. After completion of the reaction, the reaction solution was poured into 1N hydrochloric acid aqueous solution, and the thus precipitated product of interest was collected by filtration, washed with water and then dried under a reduced pressure to give 0.46 g of 2,4-dimethoxy-5-methylthiobenzoic acid.

Mass spectrometry data (m/z) EI-MS: 228 (M$^+$) Nuclear magnetic resonance spectrum (DMSO-$d_6$, TMS internal standard) δ: 2.49 (3H, s), 4.02 (3H, s), 4.07 (3H, s), 6.87 (1H, s), 7.70 (1H, s), 12.36–12.40 (1H, brs)

REFERENCE EXAMPLE 27

In the similar manner as described in Reference Example 9, 0.91 g of 2,4-dimethoxy-5-methylsulfinylbenzoic acid was obtained from 1.10 g of 2,4-dimethoxy-5-methylthiobenzoic acid.

Mass spectrometry data (m/z) EI-MS: 244 (M$^+$) Nuclear magnetic resonance spectrum (DMSO-$d_6$, TMS internal standard) δ: 2.68 (3H, s), 3.93 (3H, s), 3.97 (3H, s), 6.81 (1H, s), 8.00 (1H, s), 12.43 (1H, brs)

REFERENCE EXAMPLE 28

A 0.90 g portion of sodium sulfite and 1.81 g of sodium bicarbonate were dissolved in 6 ml of water, and 2.00 g of 5-chlorosulfonyl-2,4-dimethoxybenzoic acid was added thereto, followed by 1 hour stirring. Next, 1.50 g of bromoacetic acid was added, followed by stirring at 75° C. After completion of the reaction, the reaction solution was poured into cool water, and the thus precipitated product of interest was collected by filtration, washed with water and then dried under a reduced pressure to give 2,4-dimethoxy-5-methylsulfonylbenzoic acid, which was used in the next reaction without purification.

REFERENCE EXAMPLE 29

(1) A 1.00 g portion of methyl 2,4-dimethoxybenzoate was suspended in 0.58 ml of acetic acid, and 1.44 ml of dry trifluoroacetic acid anhydride was added under ice-cooling, followed by stirring at room temperature for 12 hours. Under ice-cooling, a saturated sodium bicarbonate aqueous solution and ethyl acetate were added, and then insoluble matter was removed by celite filtration. The thus obtained filtrate was extracted with ethyl acetate, washed with water and saturated brine and then dried over anhydrous sodium sulfate. The solvent was evaporated under a reduced pressure, and the resulting residue was purified by silica gel column chromatography (chloroform:methanol=100:1–80:1) to give 0.99 g of methyl 5-acetyl-2,4-dimethoxybenzoate.

Mass spectrometry data (m/z) EI-MS: 238 (M$^+$) Nuclear magnetic resonance spectrum (CDCl$_3$, TMS internal standard) δ: 2.57 (3H, s), 3.86 (3H, s), 3.98 (3H, s), 3.98 (3H, s), 6.47 (1H, s), 8.41 (1H, s)

(2) In the similar manner as described in Reference Example 15 (2), 0.75 g of 5-acetyl-2,4-dimethoxybenzoic acid was obtained from 0.99 g of methyl 5-acetyl-2,4-dimethoxybenzoate.

Mass spectrometry data (m/z) EI-MS: 224 (M$^+$) Nuclear magnetic resonance spectrum (DMSO-$d_6$, TMS internal standard) δ: 2.52 (3H, s), 3.95 (3H, s), 4.01 (3H, s), 6.75 (1H, s), 8.15 (1H, s), 12.20–13.70 (1H, brs)

REFERENCE EXAMPLE 30

(1) A 1.00 g portion of methyl 5-acetyl-2,4-dimethoxybenzoate was dissolved in 10 ml of methanol, and 0.24 g of sodium borohydride was added in small portions. After 10 minutes of stirring at room temperature, 1N hydrochloric acid aqueous solution was added thereto, and the thus precipitated product of interest was collected by filtration, washed with water and then dried under a reduced pressure to give 0.90 g of methyl 2,4-dimethoxy-5-(1-hydroxy)ethylbenzoate.

Mass spectrometry data (m/z) FAB-MS: 241 (M$^+$+1) Nuclear magnetic resonance spectrum (CDCl$_3$, TMS internal standard) δ: 1.49 (3H, d, J=6.5 Hz), 2.32 (1H, d, J=5.0 Hz), 3.86 (3H, s), 3.92 (3H, s), 3.93 (3H, s), 5.03–5.08 (1H, m), 6.46 (1H, s), 7.90 (1H, s)

(2) In the similar manner as described in Reference Example 15 (2), 0.77 g of 2,4-dimethoxy-5-(1-hydroxy) ethylbenzoic acid was obtained from 0.89 g of methyl 2,4-dimethoxy-5-(1-hydroxy)ethylbenzoate.

Mass spectrometry data (m/z) EI-MS: 226 (M$^+$) Nuclear magnetic resonance spectrum (DMSO-$d_6$, TMS internal standard) δ: 1.23 (3H, d, J=6.0 Hz), 3.85 (3H, s), 3.88 (3H, s), 4.70–5.20 (2H, m), 6.63 (1H, s), 7.85 (1H, s), 11.80–12.20 (H, brs)

REFERENCE EXAMPLE 31

(1) A 0.50 g portion of methyl 5-acetyl-2,4-dimethoxybenzoate was dissolved in 10 ml of trifluoroacetic acid, 0.83 ml of triethylsilane was added, followed by 20 minutes stirring. After evaporation of the solvent, the resulting residue was purified by silica gel column chromatography (hexane:ethyl acetate=3:1) to give 0.50 g of methyl 2,4-dimethoxy-5-ethylbenzoate.

Mass spectrometry data (m/z) EI-MS: 224 (M$^+$) Nuclear magnetic resonance spectrum (CDCl$_3$, TMS internal standard) δ: 1.16 (3H, d, J=7.5 Hz), 2.57 (2H, q, J=7.5 Hz), 3.86 (3H, s), 3.88 (3H, s), 3.91 (3H, s), 6.44 (1H, s), 7.67 (1H, s)

(2) In the similar manner as described in Reference Example 15 (2), 0.55 g of 2,4-dimethoxy-5-ethylbenzoic acid was obtained from 0.60 g of methyl 2,4-dimethoxy-5-ethylbenzoate.

Mass spectrometry data (m/z) EI-MS: 210 (M$^+$) Nuclear magnetic resonance spectrum (CDCl$_3$, TMS internal standard) δ: 1.17 (3H, d, J=7.5 Hz), 2.59 (2H, q, J=7.5 Hz), 3.91 (3H, s), 4.08 (3H, s), 6.47 (1H, s), 7.95 (1H, s), 10.55 (1H, brs)

REFERENCE EXAMPLE 32

A 0.44 g portion of sodium hydride (50% oily form) was washed with n-hexane and dissolved in 50 ml of dimethyl sulfoxide, and 1.64 ml of propanethiol was added dropwise. After 15 minutes of stirring at room temperature, 2.00 g of 4-chloro-2-methoxy-5-nitrobenzoic acid which has been dissolved in 20 ml of dimethyl sulfoxide was added dropwise, followed by 3 hours of stirring at room temperature. Then, 50 ml of water was added to the reaction solution, and the thus formed crystals were collected by filtration. The crystals were suspended in 50 ml of methanol, and 10 ml of 1 N hydrochloric acid was added, followed by stirring. The crystals were collected by filtration and then dried under a reduced pressure to give 0.82 g of 2-methoxy-5-nitro-4-propylthiobenzoic acid.

Mass spectrometry data (m/z) FAB-MS: 257 (M$^-$−1) Nuclear magnetic resonance spectrum (DMSO-d$_6$, TMS internal standard) δ: 1.06 (3H, t), 1.74 (2H, q), 3.14 (2H, t), 4.02 (3H, s), 7.00 (1H, s), 8.57 (1H, s), 13.15 (1H, br)

REFERENCE EXAMPLE 33

A 10 ml portion of 40% methylamine methanol solution was mixed with 500 mg of 5-nitro-4-chloro-O-anisic acid and sealed in a tube to carry out 24 hours of stirring at 50° C. The reaction solution was poured into ice water and adjusted to a pH value of around 2 with 6N hydrochloric acid, and the thus formed precipitate was collected by filtration. This was dried under a reduced pressure to give 420 mg of 2,4-bis(methylamino)-5-chlorobenzoic acid.

Mass spectrometry data (m/z) EI-MS: 255 (EI, M$^+$) Nuclear magnetic resonance spectrum (DMSO-d$_6$, TMS internal standard) δ: 2.90 (3H, d, J=5.0 Hz), 2.94 (3H, d, J=5.0 Hz), 5.58 (1H, s), 8.34–8.50 (2H, m), 8.65 (1H, s), 12.60–13.20 (1H, brs)

REFERENCE EXAMPLE 34

In an atmosphere of argon, 4.80 g of methyl 2-methoxy-4-propanoylaminobenzoate was dissolved in 50 ml of tetrahydrofuran and, at room temperature, 1.9 ml (20.2 mmol) of borane dimethylsulfide complex was added in small portions. After 1 hour of reflux, and excess reagent was decomposed with dilute hydrochloric acid under ice-cooling. The reaction solution was extracted with chloroform, the resulting organic layer was washed with water and saturated brine, dried over anhydrous sodium sulfate and concentrated under a reduced pressure. Then, the resulting residue was purified by silica gel column chromatography (chloroform:methanol=100:1) to give 3.19 g of methyl 2-methoxy-4-propylaminobenzoate. Next, in an atmosphere of argon, this compound and 2.5 ml of pyridine were dissolved in 50 ml of methylene chloride, and 2.1 ml of anhydrous trifluoroacetic acid was slowly added dropwise under ice-cooling. After 12 hours of stirring at room temperature, the reaction solution was poured in ice water, stirred for a while and then extracted with methylene chloride. The organic layer was washed with water and saturated brine, dried over anhydrous sodium sulfate and concentrated under a reduced pressure. Then, the resulting residue was purified by silica gel column chromatography (chloroform:methanol=200:1) to give 3.88 g of methyl 2-methoxy-4-(propyltrifluoroacetyl)aminobenzoate.

Mass spectrometry data (m/z) FAB-MS: 320 (M$^+$+1) Nuclear magnetic resonance spectrum (CDCl$_3$, TMS internal standard) δ: 0.93 (3H, t, J=7.5 Hz), 1.58–1.66 (2H, m), 3.71 (2H, m), 3.90 (3H, s), 3.91 (3H, s), 6.80 (1H, m), 6.85 (1H, m), 7.84 (1H, m)

REFERENCE EXAMPLE 35

A 3.70 g portion of methyl 2-methoxy-4-(propyltrifluoroacetyl)aminobenzoate was dissolved in 20 ml of concentrated sulfuric acid to which, and 1.29 g of potassium nitrate was added in small portions under ice-cooling, followed by 2 hours of stirring. The reaction solution was poured into ice water and extracted with ethyl acetate, and the resulting organic layer was washed with saturated sodium bicarbonate aqueous solution, water and saturated brine, which was then dried over anhydrous sodium sulfate. The solvent was evaporated under a reduced pressure and the resulting residue was purified by silica gel column chromatography (chloroform:methanol=100:1) to give 4.30 g of methyl 2-methoxy-5-nitro-4-(propyltrifluoroacetyl)aminobenzoate.

Mass spectrometry data (m/z) FAB-MS: 365 (FAB, M$^+$+1) Nuclear magnetic resonance spectrum (CDCl$_3$, TMS internal standard) δ: 0.94 (3H, t, J=7.5 Hz), 1.56–1.66 (2H, m), 3.18 (1H, m), 3.96 (3H, s), 4.02 (3H, s), 4.16 (1H, m), 6.87 (1H, s), 8.72 (1H, s)

REFERENCE EXAMPLE 36

A 4.30 g portion of methyl 2-methoxy-5-nitro-4-(propyltrifluoroacetyl)aminobenzoate was dissolved in 10 ml of acetonitrile, and the solution was mixed with 15 ml of 2N sodium hydroxide, followed by stirring at 60° C. for 2 hours. The reaction solution was cooled to room temperature, poured into ice water and adjusted to a pH value of around 4 using concentrated hydrochloric acid, and the thus formed precipitate was collected by filtration and dried at 50° C. under a reduced pressure to give 2.54 g of 2-methoxy-5-nitro-4-propylaminobenzoic acid as yellow powdery crystals.

Mass spectrometry data (m/z) FAM-MS: 255 (M$^+$+1) Nuclear magnetic resonance spectrum (CDCl$_3$, TMS internal standard) δ: 0.98 (3H, t, J=7.5 Hz), 1.66–1.73 (2H, m), 3.37–3.42 (2H, m), 3.93 (3H, s), 6.33 (1H, s), 8.49 (1H, t, J=5.5 Hz), 8.58 (1H, s), 12.49 (1H, brs)

REFERENCE EXAMPLE 37

A 2.0 g portion of 4-cyclopropylcarbonylamino-5-chloro-2-methoxybenzoic acid and 856 mg of potassium hydroxide were dissolved in 30 ml of methanol, and 600 mg of 10% palladium-carbon powder was added, followed by stirring at room temperature for 9 hours in an atmosphere of hydrogen. The reaction solution was filtered, and the filtrate was concentrated under a reduced pressure, diluted with 1N hydrochloric acid aqueous solution and then extracted with chloroform. The organic layer was washed with water and saturated brine in that order and dried over anhydrous sodium sulfate. Then, the solvent was evaporated under a reduced pressure and the resulting residue was washed with diethyl ether to give 1.60 g of 4-cyclopropylcarbonylamino-2-methoxybenzoic acid.

Mass spectrometry data (m/z) FAB-MS: 235 (M$^+$+1) Nuclear magnetic resonance spectrum (DMSO-d$_6$, TMS internal standard) δ: 0.81–0.84 (4H, m), 1.80 (1H, m), 3.77 (3H, s), 7.14 (1H, d, J=8.5 Hz), 7.52 (1H, s), 7.66 (1H, d, J=8.5 Hz), 10.44 (1H, s), 12.21 (1H, brs)

REFERENCE EXAMPLE 38

A 780 mg portion of 4-cyclopropylcarbonylamino-2-methoxybenzoic acid was dissolved in 10 ml of acetic anhydride and 0.5 ml of acetic acid, and 790 μl of concentrated nitric acid was slowly added to the above solution under ice-cooling, followed by 2 hours of stirring. The reaction solution was poured into ice water, and the thus formed precipitate was collected by filtration and dried under a reduced pressure to give 713 mg of 4-cyclopropylcarbonylamino-2-methoxy-5-nitrobenzoic acid.

Mass spectrometry data (m/z) FAB-MS: 281 (M$^+$+1) Nuclear magnetic resonance spectrum (DMSO-d$_6$, TMS internal standard) δ: 0.87–0.94 (4H, m), 1.95 (1H, m), 3.90 (3H, s), 7.86 (1H, s), 8.41 (1H, s), 10.75 (1H, s), 12.80 (1H, brs)

EXAMPLE 1

A 0.37 g portion of 5-chloro-4-cyclohexylamino-2-methoxybenzoic acid and 0.36 ml of triethylamine were added to 15 ml of methylene chloride and, with stirring at −30° C., 0.19 ml of ethyl chloroformate was added dropwise thereto, followed by 30 minutes of stirring at −30° C. A 0.59 g portion of (3S)-3-amino-1-(bicyclo[3.3.1]non-9-yl) pyrroridine dihydrochloride which had been dissolved in 5 ml of methylene chloride and 0.58 ml of triethylamine was added dropwise to the above reaction solution, and the mixture was slowly warmed up to room temperature, stirred for additional 3 hours and then mixed with 50 ml of saturated brine. The organic layer was again washed twice with saturated brine, dried over anhydrous sodium sulfate and then concentrated under a reduced pressure to give a crude product. This was purified by silica gel column chromatography (chloroform:methanol=100:1–10:1), converted into hydrochloride using a 4N hydrochloric acid-ethyl acetate solution and then crystallized from ethyl acetate to give 0.10 g of (S)-N-[1-(bicyclo[3.3.1]non-9-yl)-3-pyrroridinyl]-5-chloro-4-cyclohexylamino-2-methoxybenzamide monohydrochloride.

EXAMPLE 2

To 10 ml of dimethylformamide, 0.30 g of 5-chloro-2-methoxy-4-propylaminobenzoic acid, 0.38 g of (3S)-3-amino-1-(bicyclo[3.3.1]non-9-yl)pyrroridine dihydrochloride and 0.56 ml of triethylamine were added under ice-cooling, and further 0.29 ml of diphenylphosphoryl azide was added dropwise, followed by warming to room temperature with stirring. Under ice-cooling, the reaction solution was poured into ice water and extracted with ethyl acetate, and the organic layer was washed with water and saturated brine in that order and then dried over anhydrous sodium sulfate. After evaporation of the solvent, the resulting residue was purified by silica gel column chromatography (chloroform:methanol=100:1–10:1), converted into hydrochloride using a 4N hydrochloric acid-ethyl acetate solution and then crystallized from ethyl acetate to give 0.15 g of (S)-N-[1-(bicyclo[3.3.1]non-9-yl)-3-pyrroridinyl]-5-chloro-2-methoxy-4-propylaminobenzamide monohydrochloride.

The following compounds of Examples 3 to 36 were synthesized using the procedure of Example 1 or 2.

EXAMPLE 3

In the similar manner as described in Example 1, 0.16 g of (S)-N-[1-(bicyclo[3.3.1]non-9-yl]-5-chloro-2-methoxy-4-methylaminobenzamide was obtained from 0.28 g of 5-chloro-2-methoxy-4-methylaminobenzoic acid.

EXAMPLE 4

In the similar manner as described in Example 2, 0.30 g of (S)-N-[1-(bicyclo[3.3.1]non-9-yl)-3-pyrrolidinyl]-5-chloro-4-cyclopropylmethylamino-2-methoxybenzamide monohydrochloride was obtained from 0.30 g of 5-chloro-4-cyclopropylmethylamino-2-methoxybenzoic acid.

EXAMPLE 5

In the similar manner as described in Example 2, 0.28 g of (S)-N-[1-(bicyclo[3.3.1]non-9-yl)-3-pyrrolidinyl]-5-chloro-2-methoxy-4-neopentylaminobenzamide monohydrochloride was obtained from 0.25 g of 5-chloro-2-methoxy-4-neopentylaminobenzoic acid.

EXAMPLE 6

In the similar manner as described in Example 2, 0.30 g of (S)-N-[1-(bicyclo[3.3.1]non-9-yl)-3-pyrrolidinyl]-2-methoxy-4-methylthio-5-nitrobenzamide was obtained from 0.45 g of 2-methoxy-4-methylthio-5-nitrobenzoic acid.

EXAMPLE 7

In the similar manner as described in Example 2, 0.48 g of (S)-N-[1-(bicyclo[3.3.1]non-9-yl)-3-pyrrolidinyl]-2,4-dimethoxy-5-nitrobenzamide was obtained from 0.35 g of 2,4-dimethoxy-5-nitrobenzoic acid.

EXAMPLE 8

In the similar manner as described in Example 2, 0.31 g of (S)-N-[1-(bicyclo[3.3.1]non-9-yl)-3-pyrrolidinyl]-2-methoxy-4-methylsulfinyl-5-nitrobenzamide was obtained from 0.30 g of 2-methoxy-4-methylsulfinyl-5-nitrobenzoic acid.

EXAMPLE 9

In the similar manner as described in Example 2, 0.20 g of (S)-N-[1-(bicyclo[3.3.1]non-9-yl)-3-pyrrolidinyl]-2,4-dimethoxybenzamide monohydrochloride was obtained from 0.25 g of 2,4-dimethoxybenzoic acid.

EXAMPLE 10

In the similar manner as described in Example 2, 0.37 g of (S)-N-[1-(bicyclo[3.3.1]non-9-yl)-3-pyrrolidinyl]-2,4,5-trimethoxybenzamide monohydrochloride was obtained from 0.29 g of 2,4,5-trimethoxybenzoic acid.

EXAMPLE 11

In the similar manner as described in Example 2, 0.46 g of (S)-N-[1-(bicyclo[3.3.1]non-9-yl)-3-pyrrolidinyl]-2-methoxy-4-methylthiobenzamide monohydrochloride was obtained from 0.44 g of 2-methoxy-4-methylthiobenzoic acid.

EXAMPLE 12

In the similar manner as described in Example 2, 0.08 g of (S)-N-[1-(bicyclo[3.3.1]non-9-yl)-3-pyrrolidinyl]-2-methoxy-4-methylamino-5-nitrobenzamide was obtained from 0.28 g of 2-methoxy-4-methylamino-5-nitrobenzoic acid.

EXAMPLE 13

In the similar manner as described in Example 2, 0.08 g of (S)-N-[1-(bicyclo[3.3.1]non-9-yl)-3-pyrrolidinyl]-2,4-dipropoxy-5-nitrobenzamide monohydrochloride was obtained from 0.07 g of 2,4-dipropoxy-5-nitrobenzoic acid.

EXAMPLE 14

In the similar manner as described in Example 2, 0.39 g of (S)-N-[1-(bicyclo[3.3.1]non-9-yl)-3-pyrrolidinyl]-5-chloro-2,4-dimethoxybenzamide was obtained from 0.43 g of 5-chloro-2,4-dimethoxybenzoic acid.

EXAMPLE 15

In the similar manner as described in Example 2, 0.35 g of (S)-N-[1-(bicyclo[3.3.1]non-9-yl)-3-pyrrolidinyl]-2-methoxy-4-methylbenzamide monohydrochloride was obtained from 0.34 g of 2-methoxy-4-methylbenzoic acid.

EXAMPLE 16

In the similar manner as described in Example 2, 0.55 g of (S)-N-[1-(bicyclo[3.3.1]non-9-yl)-3-pyrrolidinyl]-2-methoxy-4-methyl-5-nitrobenzamide was obtained from 0.43 g of 2-methoxy-4-methyl-5-nitrobenzoic acid.

EXAMPLE 17

In the similar manner as described in Example 2, 0.38 g of (S)-N-[1-(bicyclo[3.3.1]non-9-yl)-3-pyrrolidinyl]-4-isopropoxy-2-methoxy-5-nitrobenzamide monohydrochloride was obtained from 0.40 g of 4-isopropoxy-2-methoxy-5-nitrobenzoic acid.

EXAMPLE 18

In the similar manner as described in Example 2, 0.55 g of (S)-N-[1-(bicyclo[3.3.1]non-9-yl)-3-pyrrolidinyl]-2-methoxy-5-nitro-4-propoxybenzamide monohydrochloride was obtained from 0.40 g of 2-methoxy-5-nitro-4-propoxybenzoic acid.

EXAMPLE 19

In the similar manner as described in Example 2, 0.12 g of (S)-N-[1-(bicyclo[3.3.1]non-9-yl)-3-pyrrolidinyl]-5-cyano-2,4-dimethoxybenzamide was obtained from 0.30 g of 5-cyano-2,4-dimethoxybenzoic acid.

EXAMPLE 20

In the similar manner as described in Example 2, 0.43 g of (S)-N-[1-(bicyclo[3.3.1]non-9-yl)-3-pyrrolidinyl]-4-cyclopropylmethyloxy-2-methoxy-5-nitrobenzamide was obtained from 0.42 g of 4-cyclopropylmethyloxy-2-methoxy-5-nitrobenzoic acid.

EXAMPLE 21

In the similar manner as described in Example 2, 0.21 g of (S)-4-benzyloxy-N-[1-(bicyclo[3.3.1]non-9-yl)-3-pyrrolidinyl]-2-methoxy-5-nitrobenzamide was obtained from 0.23 g of 4-benzyloxy-2-methoxy-5-nitrobenzoic acid.

EXAMPLE 22

In the similar manner as described in Example 2, 0.25 g of (S)-N-[1-(bicyclo[3.3.1]non-9-yl)-3-pyrrolidinyl]-4-cyclohexyloxy-2-methoxy-5-nitrobenzamide was obtained from 0.46 g of 4-cyclohexyloxy-2-methoxy-5-nitrobenzoic acid.

EXAMPLE 23

In the similar manner as described in Example 2, 0.22 g of 2-methoxy-5-nitro-4-propoxy-N-[(3S)-1-(8,9,10-trinorborn-2-yl)pyrrolidinyl]benzamide was obtained from 0.40 g of 2-methoxy-5-nitro-4-propoxybenzoic acid and 0.42 g of (3S)-3-amino-1-(8,9,10-trinorborn-2-yl) pyrrolidine dihydrochloride.

EXAMPLE 24

In the similar manner as described in Example 2, 0.11 g of (S)-5-amino-N-[1-(bicyclo[3.3.1]non-9-yl)-3-pyrrolidinyl]-2,4-dimethoxybenzamide monofumarate was obtained from 5-amino-2,4-dimethoxybenzoic acid.

EXAMPLE 25

In the similar manner as described in Example 2, 0.33 g of (S)-N-[1-(bicyclo[3.3.1]non-9-yl)-3-pyrrolidinyl]-5-bromo-2,4-dimethoxybenzamide was obtained from 0.41 g of 5-bromo-2,4-dimethoxybenzoic acid.

EXAMPLE 26

In the similar manner as described in Example 2, 0.38 g of (S)-N-[1-(bicyclo[3.3.1]non-9-yl)-3-pyrrolidinyl]-2-methoxy-5-nitro-4-propylthiobenzamide was obtained from 0.40 g of 2-methoxy-5-nitro-4-propylthiobenzoic acid.

EXAMPLE 27

In the similar manner as described in Example 2, 0.07 g of (S)-N-[1-(bicyclo[3.3.1]non-9-yl)-3-pyrrolidinyl]-5-cyano-2-methoxy-4-propoxybenzamide was obtained from 0.37 g of 5-cyano-2-methoxy-4-propoxybenzoic acid.

EXAMPLE 28

In the similar manner as described in Example 2, 0.52 g of (S)-N-[1-(2-adamantyl)-3-pyrrolidinyl]-5-cyano-2-methoxy-4-propoxybenzamide was obtained from 0.37 g of 5-cyano-2-methoxy-4-propoxybenzoic acid.

EXAMPLE 29

In the similar manner as described in Example 2, 0.22 g of (S)-5-aminosulfonyl-N-[1-(bicyclo[3.3.1]non-9-yl)-3-pyrrolidinyl]-2,4-dimethoxybenzamide was obtained from 0.39 g of 5-aminosulfonyl-2,4-dimethoxybenzoic acid.

EXAMPLE 30

In the similar manner as described in Example 2, 0.58 g of (S)-N-[1-(bicyclo[3.3.1]non-9-yl)-3-pyrrolidinyl]-2,4- dimethoxy-5-methylaminobenzamide hemifumarate was obtained from 2,4-dimethoxy-5-methylaminobenzoic acid.

EXAMPLE 31

In the similar manner as described in Example 2, 0.15 g of (S)-N-[1-(bicyclo[3.3.1]non-9-yl)-3-pyrrolidinyl]-2,4-dimethoxy-5-methylthiobenzamide was obtained from 0.21 g of 2,4-dimethoxy-5-methylthiobenzoic acid.

EXAMPLE 32

In the similar manner as described in Example 2, 0.16 g of (S)-N-[1-(bicyclo[3.3.1]non-9-yl)-3-pyrrolidinyl]-2,4-dimethoxy-5-methylsulfinylbenzamide was obtained from 0.40 g of 2,4-dimethoxy-5-methylsulfinylbenzoic acid.

EXAMPLE 33

In the similar manner as described in Example 2, 0.12 g of (S)-N-[1-(bicyclo[3.3.1]non-9-yl)-3-pyrrolidinyl]-2,4-dimethoxy-5-methylsulfonylbenzamide was obtained from 2,4-dimethoxy-5-methylsulfonylbenzoic acid.

EXAMPLE 34

In the similar manner as described in Example 2, 0.37 g of (S)-5-acetyl-N-[1-(bicyclo[3.3.1]non-9-yl)-3-pyrrolidinyl]-2,4-dimethoxybenzamide was obtained from 0.35 g of 5-acetyl-2,4-dimethoxybenzoic acid.

EXAMPLE 35

In the similar manner as described in Example 2, 0.30 g of (S)-N-[1-(bicyclo[3.3.1]non-9-yl)-3-pyrrolidinyl]-5-(1-hydroxyethyl)-2,4-dimethoxybenzamide was obtained from 0.36 g of 2,4-dimethoxy-5-(1-hydroxy)ethylbenzoic acid.

EXAMPLE 36

In the similar manner as described in Example 2, 0.22 g of (S)-N-[1-(bicyclo[3.3.1]non-9-yl)-3-pyrrolidinyl]-5-ethyl-2,4-dimethoxybenzamide was obtained from 0.50 g of 2,4-dimethoxy-5-ethylbenzoic acid.

EXAMPLE 37

In the similar manner as described in Example 2, (S)-N-[1-(bicyclo[3.3.1]non-9-yl)-3-pyrrolidinyl]-2,4-bis(methylamino)-5-nitrobenzamide was obtained from 2,4-bis(methylamino)-5-nitrobenzoic acid and (3S)-3-amino-1-(bicyclo[3.3.1]non-9-yl)pyrrolidine dihydrochloride.

EXAMPLE 38

A 647 mg portion of (S)-5-amino-N-[1-(bicyclo[3.3.1]non-9-yl)-3-pyrrolidinyl]-2,4-dimethoxybenzamide was dissolved in 6 ml of acetonitrile, and 1.35 ml of 37% formalin aqueous solution, 315 mg of sodium cyanoborohydride and 0.1 ml of acetic acid were added under ice-cooling, followed by stirring at room temperature for 7 hours. The reaction solution was mixed with sodium bicarbonate aqueous solution and extracted with chloroform, and the resulting organic layer was washed with water and saturated brine. The solvent was evaporated under a reduced pressure, and the resulting residue was purified by silica gel column chromatography (chloroform-methanol= 100:1–20:1) to give 572 mg of a yellow oily material. This was dissolved in ethanol and mixed with 76 mg of fumaric acid, and the thus formed precipitate was collected by filtration to give 313 mg of (S)-N-[1-(bicyclo[3.3.1]non-9-yl)-3-pyrrolidinyl]-5-dimethylamino-2,4-dimethoxybenzamide monofumarate.

EXAMPLE 39

In the similar manner as described in Example 2, 450 mg of (S)-4-amino-N-[1-(bicyclo[3.3.1]non-9-yl)-3-pyrrolidinyl]-2-methoxy-5-nitrobenzamide was synthesized from 400 mg of 4-amino-2-methoxy-5-nitrobenzoic acid and 624 mg of (3S)-3-amino-1-(bicyclo[3.3.1]non-9-yl) pyrrolidine dihydrochloride.

EXAMPLE 40

In the similar manner as described in Example 2, 622 mg of (S)-N-[1-(bicyclo[3.3.1]non-9-yl)-3-pyrrolidinyl]-2-methoxy-5-nitro-4-propylaminobenzamide was synthesized from 500 mg of 2-methoxy-5-nitro-4-propylaminobenzoic acid and 582 mg of (3S)-3-amino-1-(bicyclo[3.3.1]non-9-yl)pyrrolidine. dihydrochloride.

EXAMPLE 41

In the similar manner as described in Example 2, 276 mg of (S)-N-[1-(bicyclo[3.3.1]non-9-yl)-3-pyrrolidinyl]-4-cyclopropylcarbonylamino-2-methoxy-5-nitrobenzamide was synthesized from 321 mg of 4-cyclopropylcarbonylamino-2-methoxy-5-nitrobenzoic acid and 355 mg of (3S)-3-amino-1-(bicyclo[3.3.1]non-9-yl)pyrrolidine dihydrochloride.

Chemical structures and physicochemical properties of the compounds obtained in the above Examples are shown in the following Table 4.

TABLE 4

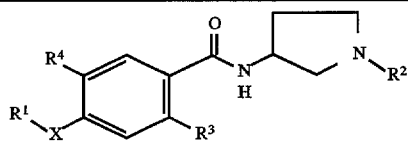

| Example No. | $R^1$ | X | $R^2$ | $R^3$ | $R^4$ | Physicochemical Properties |
|---|---|---|---|---|---|---|
| 1 | (cyclohexyl) | NH | (bicyclononyl) | —OCH$_3$ | Cl | Melting point: 212–217° C.<br>Elemental analysis: C$_{27}$H$_{40}$N$_3$O$_2$Cl.HCl –0.5H$_2$O<br><br>          C %   H %    N %   Cl %<br>Measured   62.42   8.15   8.09   13.65<br>Calcd.        62.43   8.05   8.30   13.80 |

TABLE 4-continued

Structure:

$R^4$, $R^1$-X- on benzene ring with $R^3$, benzamide -C(=O)-NH- connected to pyrrolidine with N-$R^2$

| Example No. | $R^1$ | X | $R^2$ | $R^3$ | $R^4$ | Physicochemical Properties |
|---|---|---|---|---|---|---|
| | | | | | | Mass analysis: (m/z) 474 (FAB, M$^+$ +1) |
| 2 | —C$_3$H$_7$ | NH | (bicyclic) | —OCH$_3$ | Cl | Melting point: 195–203° C. Elemental analysis: C$_{24}$H$_{36}$N$_3$O$_2$Cl·HCl<br><br>  C% H% N% Cl%<br>Measured 61.27 7.93 8.93 15.07<br>Calcd.   61.05 8.05 8.91 14.80<br>Mass analysis: (m/z) 434 (FAB, M$^+$ +1) |
| 3 | —CH$_3$ | NH | (bicyclic) | —OCH$_3$ | Cl | Melting point: 183–184° C. Elemental analysis: C$_{22}$H$_{32}$N$_3$O$_2$Cl<br><br>  C% H% N% Cl%<br>Measured 65.09 7.94 10.35 8.73<br>Calcd.   64.96 7.99 10.34 8.91<br>Mass analysis: (m/z) 406 (FAB, M$^+$ +1) |
| 4 | —CH$_2$-cyclopropyl | NH | (bicyclic) | —OCH$_3$ | Cl | Melting point: 200–205° C. Elemental analysis: C$_{25}$H$_{36}$N$_3$O$_2$Cl·HCl·0.6H$_2$O<br><br>  C% H% N% Cl%<br>Measured 60.87 7.81 8.52 14.37<br>Calcd.   60.72 7.59 8.56 14.35<br>Mass analysis: (m/z) 446 (FAB, M$^+$ +1) |
| 5 | —CH$_2$—C(CH$_3$)$_3$ | NH | (bicyclic) | —OCH$_3$ | Cl | Melting point: 210–231° C. Elemental analysis: C$_{26}$H$_{40}$N$_3$O$_2$Cl·HCl<br><br>  C% H% N% Cl%<br>Measured 62.64 8.29 8.43 14.22<br>Calcd.   62.30 8.30 8.36 14.23<br>Mass analysis: (m/z) 462 (FAB, M$^+$ +1) |
| 6 | —CH$_3$ | S | (bicyclic) | —OCH$_3$ | NO$_2$ | Melting point: 176–179° C. Elemental analysis: C$_{22}$H$_{31}$N$_3$O$_4$S<br><br>  C% H% N% S%<br>Measured 60.95 7.21 9.69 7.40<br>Calcd.   60.79 7.09 9.60 7.45<br>Mass analysis: (m/z) 434 (FAB, M$^+$ +1) |
| 7 | —CH$_3$ | O | (bicyclic) | —OCH$_3$ | NO$_2$ | Melting point: 225–229° C. Elemental analysis: C$_{22}$H$_{31}$N$_3$O$_5$·0.2H$_2$O<br><br>  C% H% N%<br>Measured 62.75 7.52 9.98<br>Calcd.   62.85 7.36 10.12<br>Mass analysis: (m/z) 418 (FAB, M$^+$ +1) |
| 8 | —CH$_3$ | SO | (bicyclic) | —OCH$_3$ | NO$_2$ | Melting point: 176–188° C. Elemental analysis: C$_{22}$H$_{31}$N$_3$O$_6$S<br><br>  C% H% N% S%<br>Measured 58.78 6.95 9.35 7.13<br>Calcd.   58.50 6.95 9.26 6.84<br>Mass analysis: (m/z) 450 (FAB, M$^+$ +1) |

TABLE 4-continued

| Example No. | R¹ | X | R² | R³ | R⁴ | Physicochemical Properties |
|---|---|---|---|---|---|---|
| 9 | —CH₃ | O | (bicyclic) | —OCH₃ | —OCH₃ | Melting point: 214–217° C.<br>Elemental analysis: $C_{22}H_{32}N_2O_3 \cdot HCl$<br><br>        C %  H %  N %  Cl %<br>Measured  64.61  8.13  6.85  8.67<br>Calcd.      64.36  8.24  6.80  8.64<br>Mass analysis: (m/z) 373 (FAB, M⁺ +1) |
| 10 | —CH₃ | O | (bicyclic) | —OCH₃ | —OCH₃ | Melting point: 234–240° C.<br>Elemental analysis: $C_{22}H_{34}N_2O_4 \cdot HCl - 0.5H_2O$<br><br>        C %  H %  N %  Cl %<br>Measured  61.66  8.10  6.25  7.91<br>Calcd.      61.59  8.00  6.14  7.99<br>Mass analysis: (m/z) 403 (FAB, M⁺ +1) |
| 11 | —CH₃ | S | (bicyclic) | —OCH₃ | H | Melting point: 226–228° C.<br>Elemental analysis: $C_{22}H_{32}N_2O_2S \cdot HCl - 0.1H_2O$<br><br>        C %  H %  N %  S %  Cl %<br>Measured  61.91  7.84  6.56  7.51  8.31<br>Calcd.      61.86  7.73  6.59  7.45  8.36<br>Mass analysis: (m/z) 389 (FAB, M⁺ +1) |
| 12 | —CH₃ | NH | (bicyclic) | —OCH₃ | NO₂ | Melting point: 225–229° C.<br>Elemental analysis: $C_{22}H_{32}N_4O_4$<br><br>        C %  H %  N %<br>Measured  63.44  7.74  13.45<br>Calcd.      63.19  7.84  13.26<br>Mass analysis: (m/z) 417 (FAB, M⁺ +1) |
| 13 | —C₃H₇ | O | (bicyclic) | —OC₃H₇ | NO₂ | Melting point: 223–230° C.<br>Elemental analysis: $C_{26}H_{39}N_3O_5 \cdot HCl - 0.2H_2O$<br><br>        C %  H %  N %  Cl %<br>Measured  60.79  7.93  8.18  6.90<br>Calcd.      60.79  7.91  8.13  6.83<br>Mass analysis: (m/z) 474 (FAB, M⁺ +1) |
| 14 | —CH₃ | O | (bicyclic) | —OCH₃ | Cl | Melting point: 165–169° C.<br>Elemental analysis: $C_{22}H_{31}N_2O_3Cl$<br><br>        C %  H %  N %  Cl %<br>Measured  64.93  7.68  6.88  8.71<br>Calcd.      64.83  7.59  6.87  8.72<br>Mass analysis: (m/z) 407 (FAB, M⁺ +1) |
| 15 | —CH₃ | Bond | (bicyclic) | —OCH₃ | H | Melting point: 244–246° C.<br>Elemental analysis: $C_{22}H_{32}N_2O_2 \cdot HCl - 0.3H_2O$<br><br>        C %  H %  N %  Cl %<br>Measured  66.33  8.50  7.03  8.90<br>Calcd.      66.30  8.43  7.02  8.76<br>Mass analysis: (m/z) 357 (FAB, M⁺ +1) |

TABLE 4-continued

| Example No. | R¹ | X | R² | R³ | R⁴ | Physicochemical Properties |
|---|---|---|---|---|---|---|
| 16 | —CH₃ | Bond | (cyclohexyl) | —OCH₃ | NO₂ | Melting point: 160–161° C.<br>Elemental analysis: $C_{22}H_{31}N_3O_4$<br><br>         C %   H %   N %<br>Measured   65.81   7.78   10.47<br>Calcd.       65.71   7.77   10.48<br>Mass analysis: (m/z) 402 (FAB, M⁺ +1) |
| 17 | —CH(CH₃)₂ | O | (cyclohexyl) | —OCH₃ | NO₂ | Melting point: 161–164° C.<br>Elemental analysis: $C_{24}H_{35}N_3O_5 \cdot HCl - H_2O$<br><br>         C %   H %   N %   Cl %<br>Measured   57.65   7.66   8.40   7.09<br>Calcd.       57.66   7.51   8.31   6.91<br>Mass analysis: (m/z) 446 (FAB, M⁺ +1) |
| 18 | —C₃H₇ | O | (cyclohexyl) | —OCH₃ | NO₂ | Melting point: 157–163° C.<br>Elemental analysis: $C_{24}H_{35}N_3O_5 \cdot HCl \cdot 0.8H_2O$<br><br>         C %   H %   N %   Cl %<br>Measured   58.07   7.63   8.46   7.14<br>Calcd.       57.91   7.52   8.46   7.20<br>Mass analysis: (m/z) 446 (FAB, M⁺ +1) |
| 19 | —CH₃ | O | (cyclohexyl) | —OCH₃ | CN | Melting point: 206–212° C.<br>Elemental analysis: $C_{23}H_{31}N_3O_3 \cdot 0.2H_2O$<br><br>         C %   H %   N %<br>Measured   68.87   7.89   10.48<br>Calcd.       68.99   7.88   10.49<br>Mass analysis: (m/z) 398 (FAB, M⁺ +1) |
| 20 | —CH₂—(cyclopropyl) | O | (cyclohexyl) | —OCH₃ | NO₂ | Melting point: 167–170° C.<br>Elemental analysis: $C_{25}H_{36}N_3O_6 \cdot 0.1H_2O$<br><br>         C %   H %   N %<br>Measured   65.37   7.72   9.15<br>Calcd.       65.27   7.73   9.16<br>Mass analysis: (m/z) 458 (FAB, M⁺ +1) |
| 21 | —CH₂—(phenyl) | O | (cyclohexyl) | —OCH₃ | NO₂ | Melting point: 174–178° C.<br>Elemental analysis: $C_{23}H_{35}N_3O_5$<br><br>         C %   H %   N %<br>Measured   68.13   7.14   8.51<br>Calcd.       67.94   7.18   8.54<br>Mass analysis: (m/z) 494 (FAB, M⁺ +1) |
| 22 | (cyclohexyl) | O | (cyclohexyl) | —OCH₃ | NO₂ | Melting point: 87–92° C.<br>Elemental analysis: $C_{27}H_{39}N_3O_5 \cdot 1.1H_2O$<br><br>         C %   H %   N %<br>Measured   64.16   8.22   8.31<br>Calcd.       64.01   8.33   8.24<br>Mass analysis: (m/z) 486 (FAB, M⁺ +1) |

TABLE 4-continued

| Example No. | R¹ | X | R² | R³ | R⁴ | Physicochemical Properties |
|---|---|---|---|---|---|---|
| 23 | —C₃H₇ | O | (bicyclo[2.2.2]octyl) | —OCH₃ | NO₂ | Melting point: 120–123° C.<br>Elemental analysis: $C_{22}H_{31}N_3O_5 \cdot 0.2H_2O$<br><br>          C %  H %  N %<br>Measured  62.75  7.52  9.98<br>Calcd.      62.63  7.56  10.00<br>Mass analysis: (m/z) 418 (FAB, M⁺ +1) |
| 24 | —CH₃ | O | (bicyclohexyl) | —OCH₃ | NH₂ | Melting point: 195–200° C.<br>Elemental analysis: $C_{22}H_{33}N_3O_3 \cdot C_4H_4O_4 \cdot 0.5H_2O$<br><br>          C %  H %  N %<br>Measured  60.92  7.47  8.20<br>Calcd.      60.61  7.20  8.02<br>Mass analysis: (m/z) 388 (FAB, M⁺ +1) |
| 25 | —CH₃ | O | (bicyclohexyl) | —OCH₃ | Br | Melting point: 173–178° C.<br>$C_{22}H_{31}N_2O_3Br$<br><br>          C %  H %  N %  Br %<br>Measured  58.54  6.92  6.21  17.70<br>Calcd.      58.73  7.09  6.15  17.40<br>Mass analysis: (m/z) 451 (FAB, M⁺ +1) |
| 26 | —C₃H₇ | S | (bicyclohexyl) | —OCH₃ | NO₂ | Melting point: 129–130° C.<br>Elemental analysis: $C_{24}H_{35}N_3O_4S$<br><br>          C %  H %  N %  S %<br>Measured  62.45  7.64  9.10  6.95<br>Calcd.      62.26  7.60  9.02  7.04<br>Mass analysis: (m/z) 462 (FAB, M⁺ +1) |
| 27 | —C₃H₇ | O | (bicyclohexyl) | —OCH₃ | CN | Melting point: 147–150° C.<br>Elemental analysis: $C_{25}H_{35}N_3O_3 \cdot 0.2H_2O$<br><br>          C %  H %  N %<br>Measured  69.97  8.31  9.79<br>Calcd.      69.88  8.22  9.82<br>Mass analysis: (m/z) 426 (FAB, M⁺ +1) |
| 28 | —C₃H₇ | O | (adamantyl) | —OCH₃ | CN | Melting point: 172–177° C.<br>Elemental analysis: $C_{26}H_{35}N_3O_3 \cdot 0.3H_2O$<br><br>          C %  H %  N %<br>Measured  70.50  8.10  9.49<br>Calcd.      70.58  7.97  9.55<br>Mass analysis: (m/z) 438 (FAB, M⁺ +1) |
| 29 | —CH₃ | O | (bicyclohexyl) | —OCH₃ | —SO₂NH₂ | Melting point: 245–250° C.<br>Elemental analysis: $C_{22}H_{33}N_3O_6S \cdot 0.8H_2O$<br><br>          C %  H %  N %  S %<br>Measured  56.70  7.48  9.02  6.88<br>Calcd.      56.58  7.36  8.91  7.13<br>Mass analysis: (m/z) 452 (FAB, M⁺ +1) |

TABLE 4-continued

| Example No. | R¹ | X | R² | R³ | R⁴ | Physicochemical Properties |
|---|---|---|---|---|---|---|
| 30 | —CH₃ | O | (bicyclic) | —OCH₃ | —NHCH₂ | Melting point: amorphous<br>Elemental analysis: $C_{23}H_{35}N_3O_3 \cdot 0.5C_4H_4O_4 \cdot 0.5H_2O$<br><br>          C %  H %  N %<br>Measured  64.08  8.17  8.97<br>Calcd.     63.85  8.27  8.64<br>Mass analysis: (m/z) 402 (FAB, M⁺ +1) |
| 31 | —CH₃ | O | (bicyclic) | —OCH₃ | —SCH₃ | Melting point: 120–123° C.<br>Elemental analysis: $C_{23}H_{34}N_2O_3S \cdot 0.4H_2O$<br><br>          C %  H %  N %  S %<br>Measured  64.88  8.24  6.58  7.53<br>Calcd.     65.03  8.22  6.52  7.63<br>Mass analysis: (m/z) 419 (FAB, M⁺ +1) |
| 32 | —CH₃ | O | (bicyclic) | —OCH₃ | —SOCH₃ | Melting point: 213–220° C.<br>$C_{23}H_{34}N_2O_4S \cdot 0.7H_2O$<br><br>          C %  H %  N %  S %<br>Measured  61.77  7.98  6.26  7.17<br>Calcd.     61.48  7.65  6.22  7.54<br>Mass analysis: (m/z) 435 (FAB, M⁺ +1) |
| 33 | —CH₃ | O | (bicyclic) | —OCH₃ | —SO₂CH₃ | Melting point: 197–201° C.<br>Elemental analysis: $C_{23}H_{34}N_2O_5S$<br><br>          C %  H %  N %  S %<br>Measured  61.31  7.61  6.22  7.12<br>Calcd.     61.03  7.58  6.16  7.12<br>Mass analysis: (m/z) 451 (FAB, M⁺ +1) |
| 34 | —CH₃ | O | (bicyclic) | —OCH₃ | —COCH₃ | Melting point: 218–226° C.<br>Elemental analysis: $C_{24}H_{34}N_2O_4$<br><br>          C %  H %  N %<br>Measured  69.54  8.27  6.76<br>Calcd.     69.75  8.30  6.76<br>Mass analysis: (m/z) 415 (FAB, M⁺ +1) |
| 35 | —CH₃ | O | (bicyclic) | —OCH₃ | —CHCH₃<br>   \|<br>   OH | Melting point: 168–173° C.<br>Elemental analysis: $C_{24}H_{36}N_2O_4$<br><br>          C %  H %  N %<br>Measured  69.20  8.71  6.72<br>Calcd.     69.30  8.76  6.71<br>Mass analysis: (m/z) 417 (FAB, M⁺ +1) |
| 36 | —CH₃ | O | (bicyclic) | —OCH₃ | —C₂H₅ | Melting point: 133–135° C.<br>Elemental analysis: $C_{24}H_{36}N_2O_3$<br><br>          C %  H %  N %<br>Measured  71.96  9.06  6.99<br>Calcd.     71.90  9.12  6.93<br>Mass analysis: (m/z) 401 (FAB, M⁺ +1) |

TABLE 4-continued $$\text{R}^4\text{-}\underset{\text{R}^1-X}{\overset{}{\bigcirc}}\text{-}\underset{\text{R}^3}{\overset{O}{\text{C}}}\text{-}\underset{H}{N}\text{-}\overset{}{\underset{}{\bigcap}}\text{N-R}^2$$

| Example No. | $R^1$ | X | $R^2$ | $R^3$ | $R^4$ | Physicochemical Properties |
|---|---|---|---|---|---|---|
| 37 | —CH$_3$ | NH | (bicyclic) | —NHCH$_3$ | NO$_2$ | Melting point: 193–196° C.<br>Elemental analysis: C$_{22}$H$_{33}$N$_5$O$_3$.0.4H$_2$O<br><br>        C %  H %  N %<br>Measured  62.51  8.06  16.57<br>Calcd.      62.88  7.92  16.79<br>Mass analysis: (m/z) 416 (FAB, M$^+$ +1) |
| 38 | —CH$_3$ | O | (bicyclic) | —OCH$_3$ | —N(CH$_3$)$_2$ | Melting point: 166–169° C.<br>Elemental analysis: C$_{24}$H$_{37}$N$_3$O$_3$.C$_4$H$_4$O$_4$.0.3H$_2$O<br><br>        C %  H %  N %<br>Measured  62.62  7.81  7.82<br>Calcd.      62.58  7.76  7.81<br>Mass analysis: (m/z) 416 (FAB, M$^+$ +1) |
| 39 | H | NH | (bicyclic) | —OCH$_3$ | NO$_2$ | Melting point: 272–274° C.<br>Elemental analysis: C$_{21}$H$_{30}$N$_4$O$_4$.0.2H$_2$O<br><br>        C %  H %  N %<br>Measured  62.11  7.55  13.80<br>Calcd.      61.99  7.52  13.80<br>Mass analysis: (m/z) 403 (FAB, M$^+$ +1) |
| 40 | —C$_3$H$_7$ | NH | (bicyclic) | —OCH$_3$ | NO$_2$ | Melting point: 189–191° C.<br>Elemental analysis: C$_{24}$H$_{36}$N$_4$O$_4$<br><br>        C %  H %  N %<br>Measured  64.84  8.16  12.60<br>Calcd.      64.61  8.23  12.61<br>Mass analysis: (m/z) 445 (FAB, M$^+$ +1) |
| 41 | cyclopropyl | CONH | (bicyclic) | —OCH$_3$ | NO$_2$ | Melting point: 189–191° C.<br>Elemental analysis: C$_{26}$H$_{34}$N$_4$O$_5$<br><br>        C %  H %  N %<br>Measured  63.81  7.28  11.91<br>Calcd.      63.54  7.26  11.79<br>Mass analysis: (m/z) 471 (FAB, M$^+$ +1) |

Formulation Examples

The following illustrates Formulation Examples of the compound of the present invention as pharmaceutical drugs.

| 1) | (mg) |
|---|---|
| Invention compound | 10.0 |
| Lactose | 109.6 |
| Microcrystalline cellulose | 27.4 |
| Light anhydrous silicic acid | 1.5 |
| Magnesium stearate | 1.5 |

Using a DC type mixer, 30 g of the compound of the present invention was mixed with 328.8 g of lactose and 82.2 g of microcrystalline cellulose. The mixture was applied to a roller compactor to effect compression molding, thereby obtaining a flaky compressed material. The flaky compressed material was pulverized using a hammer mill, and the pulverized material was screened through a 20 mesh screen. To the thus screened material were added 4.5 g of light anhydrous silicic acid and 4.5 g of magnesium stearate, followed by mixing in the DC type mixer. The resulting mixture was applied to a tablet making machine using a die-punch of 7.5 mm in diameter, thereby obtaining 3,000 tablets each having a weight of 150 mg.

| 2) | (mg) |
|---|---|
| Invention compound | 10.0 |
| Lactose | 91.7 |
| Corn starch | 39.3 |
| Polyvinyl pyrrolidone K25 | 7.5 |
| Magnesium stearate | 1.5 |
| Hydroxypropylmethylcellulose 2910 | 2.3 |

-continued

| 2) | (mg) |
|---|---|
| Polyethylene glycol 6000 | 0.4 |
| Titanium dioxide | 1.1 |
| Purified talc | 0.7 |

A 30 g portion of the compound of the present invention was mixed with 275.1 g of lactose and 117.9 g of corn starch in a fluidized bed granulating machine. Separately, 22.5 g of polyvinyl pyrrolidine was dissolved in 127.5 g of water to prepare a binding solution. Using the fluidized bed granulating machine, the binding solution was sprayed to the above mixture to give granules. A 4.5 g portion of magnesium stearate was added to the thus obtained granules, followed by mixing in the DC type mixer. The resulting mixture was applied to a tablet making machine using a die-punch of 7.5 mm in diameter, thereby obtaining 3,000 tablets each having a weight of 150 mg.

Separately, a coating liquid was prepared by suspending 2.3 g of hydroxypropylmethylcellulose 2910, 0.4 g of polyethylene glycol 6000, 1.1 g of titanium dioxide and 0.7 g of purified talc in 24.2 g of water. Using a high coater, 3,000 tablets obtained above were coated with the coating liquid to give film coated tablets each having a weight of 154.5 mg.

We claim:

1. A novel N-(3-pyrrolidinyl)benzamide compound represented by a general formula (I), or a pharmaceutically acceptable salt thereof,

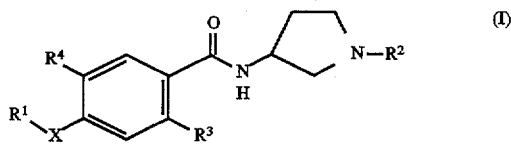

wherein each symbol in the formula has the following meaning, $R^1$: a hydrogen atom, a lower alkyl group, an aralkyl group or a cycloalkyl or cycloalkyl-lower alkyl group having 3 to 8 ring atoms, $R^2$: a bicyclic or tricyclic bridged hydrocarbon ring group having 4 to 16 ring atoms, which may be substituted by a lower alkyl group(s), $R^3$: a lower alkoxy group, an amino group or a mono- or di-lower alkylamino group, $R^4$: a hydrogen atom, a halogen atom, a lower alkyl group which may be substituted by a hydroxyl group, a lower alkoxy group, a cyano group, a nitro group, an amino group, a mono- or di-lower alkylamino group, an acyl group or a group represented by $-S(O)_m-R^5$, $R^5$: a lower alkyl group, an amino group or a mono- or di-lower alkylamino group, m: 0, 1 or 2, X: a bond or a group represented by $-O-$, $-S(O)_n-$, $-NH-$ or $-CONH-$, and n: 0, 1 or 2, with the proviso that, when $R^1$ is a cycloalkyl group, the cases wherein X is a group represented by $-CONH-$, $R^3$ is a lower alkoxy group and $R^4$ is a halogen atom are excluded.

2. The compound according to claim 1, wherein the group $R^1$ is a lower alkyl group or a cycloalkyl or cycloalkyl-lower alkyl group having 3 to 8 ring atoms, the group $R^3$ is a lower alkoxy group and the group $R^4$ is a halogen atom, cyano group or nitro group.

3. The compound according to claim 2, wherein the group $R^2$ is a bicyclononyl group or an adamantyl group.

4. The compound according to any one of claims 1 to 3, wherein it is (i) an optical isomer, (ii) an endo-exo isomer and (iii) an optical isomer and an endo-exo isomer.

5. N-[1-(Bicyclo[3.3.1]non-9-yl)-3-pyrrolidinyl]-2,4-dimethoxy-5-nitrobenzamide or a pharmaceutically acceptable salt thereof or an optical isomer thereof.

6. N-[1-(Bicyclo[3.3.1]non-9-yl)-3-pyrrolidinyl]-2-methoxy-4-methyl-5-nitrobenzamide or a pharmaceutically acceptable salt thereof or an optical isomer thereof.

7. N-[1-(Bicyclo[3.3.1]non-9-yl)-3-pyrrolidinyl]-5-cyano-2,4-dimethoxybenzamide or a pharmaceutically acceptable salt thereof or an optical isomer thereof.

8. N-[1-(Bicyclo[3.3.1]non-9-yl)-3-pyrrolidinyl]-2,4-dimethoxy-5-methylaminobenzamide or a pharmaceutically acceptable salt thereof or an optical isomer thereof.

9. A pharmaceutical composition which comprises the N-(3-pyrrolidinyl)benzamide compound of any one of claims 1 to 8 or a pharmaceutically acceptable salt thereof or an isomer thereof and a pharmaceutically acceptable carrier.

10. A dopamine $D_3$ receptor antagonist, a $D_4$ receptor antagonist or a $D_3$ and $D_4$ receptor antagonist, which comprises the N-(3-pyrrolidinyl)benzaminde derivative of any one of claims 1 to 3 or a pharmaceutically acceptable salt thereof or an isomer thereof as an active ingredient.

11. The dopamine $D_3$ receptor antagonist, $D_4$ receptor antagonist or $D_3$ and $D_4$ receptor antagonist according to claim 10, wherein it is a psychotropic agent.

12. The dopamine $D_3$ receptor antagonist, $D_4$ receptor antagonist or $D_3$ and $D_4$ receptor antagonist according to claim 10, wherein it is a schizophrenia-treating agent.

* * * * *